United States Patent
Ferragamo et al.

(10) Patent No.: US 10,085,735 B2
(45) Date of Patent: Oct. 2, 2018

(54) MODULAR TISSUE REPAIR KIT AND DEVICES AND METHOD RELATED THERETO

(71) Applicant: Smith & Nephew, Inc., Memphis, TN (US)

(72) Inventors: Michael C. Ferragamo, Foster, RI (US); William R. Davis, Hingham, MA (US)

(73) Assignee: Smith & Nephew, Inc., Memphis, TN (US)

( * ) Notice: Subject to any disclaimer, the term of this patent is extended or adjusted under 35 U.S.C. 154(b) by 425 days.

(21) Appl. No.: 14/526,857

(22) Filed: Oct. 29, 2014

(65) Prior Publication Data
US 2016/0120535 A1    May 5, 2016

(51) Int. Cl.
*A61B 17/04*    (2006.01)
*A61B 17/06*    (2006.01)
*A61B 17/00*    (2006.01)

(52) U.S. Cl.
CPC ...... *A61B 17/0401* (2013.01); *A61B 17/0467* (2013.01); *A61B 2017/00473* (2013.01);
(Continued)

(58) Field of Classification Search
CPC ................. A61F 2/2457; A61F 2/2454; A61F 2002/304411; A61F 2/08111;
(Continued)

(56) References Cited

U.S. PATENT DOCUMENTS

| 4,333,596 | A | * | 6/1982 | Kunreuther | ............. B65C 7/005 |
|---|---|---|---|---|---|
| | | | | | 227/67 |
| 5,928,252 | A | | 7/1999 | Steadman et al. | |

(Continued)

FOREIGN PATENT DOCUMENTS

| WO | 1995015726 A1 | 6/1995 |
|---|---|---|
| WO | 2007124773 A1 | 11/2007 |

(Continued)

OTHER PUBLICATIONS

International Search Report and Written Opinion for related International Application No. PCT/US2014/062797 dated Jun. 24, 2015.
(Continued)

*Primary Examiner* — David C Eastwood
(74) *Attorney, Agent, or Firm* — Burns & Levinson, LLP; Joseph M. Maraia

(57) ABSTRACT

Featured is an implant/anchor deployment device/module, a device kit concept using such an implant/anchor deployment device/module, a system for deploying an implant/anchor into tissue, and a method for treating damaged tissue using such an implant/anchor deployment device/module such as for example, a method for deploying one or more anchors/implants during a meniscal repair procedure. Such a deployment device/module includes a body member having a proximal end portion and a distal end portion, the distal end portion being configured so that an implant/anchor can be deployed therefrom. Also, the proximal end portion is configured so as to be removably attached to a first end portion of the surgical device. In exemplary embodiments, the surgical device includes a suture cutter as known in the endoscopy arts.

16 Claims, 8 Drawing Sheets

(52) U.S. Cl.
CPC ............... *A61B 2017/0409* (2013.01); *A61B 2017/0417* (2013.01); *A61B 2017/06052* (2013.01)

(58) Field of Classification Search
CPC .......... A61B 17/0487; A61B 17/04011; A61B 2017/00575; A61B 17/10; A61B 2017/0409; A61B 2017/0408; A61B 2017/0416; A61B 2017/0417; A61B 2017/042; A61B 2017/04221; A61B 2017/04241; A61B 17/04661; A61B 2017/0454
See application file for complete search history.

(56) References Cited

U.S. PATENT DOCUMENTS

| | | | |
|---|---|---|---|
| 5,941,439 A * | 8/1999 | Kammerer | A61B 17/068 227/175.1 |
| 6,059,719 A * | 5/2000 | Yamamoto | A61B 1/00059 600/104 |
| 6,156,044 A | 12/2000 | Kammerer et al. | |
| 6,543,456 B1 * | 4/2003 | Freeman | A61B 17/1114 128/898 |
| 6,626,916 B1 * | 9/2003 | Yeung | A61B 17/0401 606/139 |
| 7,179,267 B2 * | 2/2007 | Nolan | A61B 17/1114 227/175.1 |
| 7,651,509 B2 * | 1/2010 | Bojarski | A61B 17/0401 606/139 |
| 8,128,640 B2 | 3/2012 | Harris et al. | |
| 8,808,309 B2 * | 8/2014 | Nelson | A61B 17/0401 606/139 |
| 9,402,616 B2 | 8/2016 | Harris et al. | |
| 2001/0010005 A1 * | 7/2001 | Kammerer | A61B 17/064 606/151 |
| 2002/0019649 A1 * | 2/2002 | Sikora | A61B 17/0401 606/232 |
| 2002/0116012 A1 * | 8/2002 | May | A61B 17/0469 606/148 |
| 2002/0188301 A1 | 12/2002 | Powell | |
| 2004/0116949 A1 * | 6/2004 | Ewers | A61B 17/00234 606/167 |
| 2004/0162568 A1 * | 8/2004 | Saadat | A61B 1/00135 606/139 |
| 2004/0220573 A1 | 11/2004 | McDevitt | |
| 2004/0249392 A1 * | 12/2004 | Mikkaichi | A61B 17/0469 606/142 |
| 2005/0033363 A1 | 2/2005 | Bojarski | |
| 2005/0251205 A1 * | 11/2005 | Ewers | A61B 17/0401 606/232 |
| 2005/0261710 A1 * | 11/2005 | Sakamoto | A61B 17/0401 606/139 |
| 2005/0283192 A1 | 12/2005 | Bojarski | |
| 2006/0009765 A1 * | 1/2006 | Martinek | A61B 17/0682 606/139 |
| 2006/0030884 A1 * | 2/2006 | Yeung | A61B 17/0401 606/232 |
| 2007/0027476 A1 * | 2/2007 | Harris | A61B 17/0401 606/232 |
| 2007/0073316 A1 * | 3/2007 | Sgro | A61B 17/064 606/151 |
| 2007/0112338 A1 * | 5/2007 | Cohen | A61B 17/0401 606/1 |
| 2007/0149987 A1 * | 6/2007 | Wellman | A61B 17/0057 606/148 |
| 2007/0270907 A1 * | 11/2007 | Stokes | A61B 17/0469 606/232 |
| 2007/0288023 A1 * | 12/2007 | Pellegrino | A61B 17/0401 606/232 |
| 2008/0086152 A1 * | 4/2008 | McKay | A61B 17/0469 606/139 |
| 2008/0208218 A1 * | 8/2008 | Shiono | A61B 17/0401 606/144 |
| 2008/0208219 A1 * | 8/2008 | Suzuki | A61B 17/0401 606/144 |
| 2009/0182354 A1 * | 7/2009 | Blier | A61B 17/07207 606/148 |
| 2010/0106169 A1 | 4/2010 | Niese | |
| 2014/0088646 A1 * | 3/2014 | Wales | A61B 17/0401 606/232 |
| 2014/0142689 A1 * | 5/2014 | De Canniere | A61F 2/2457 623/2.11 |
| 2014/0288600 A1 | 9/2014 | Yeung et al. | |
| 2014/0305988 A1 * | 10/2014 | Boudreaux | A61B 17/068 227/175.3 |
| 2015/0133997 A1 * | 5/2015 | Deitch | A61B 17/0401 606/228 |
| 2015/0190129 A1 | 7/2015 | Nelson et al. | |
| 2017/0027557 A1 | 2/2017 | Harris et al. | |

FOREIGN PATENT DOCUMENTS

| | | |
|---|---|---|
| WO | 2013163173 A1 | 10/2013 |
| WO | 2014043703 A1 | 3/2014 |

OTHER PUBLICATIONS

EP Office Action app No. 09764137.7 dated Aug. 16, 2017, 6 pages.
IPRP for PCT app No. PCT/US16/016572 dated Aug. 8, 2017, 7 pages.
AU Office Action for app No. 2016200856 dated Jun. 9, 2017, 5 pages.

* cited by examiner

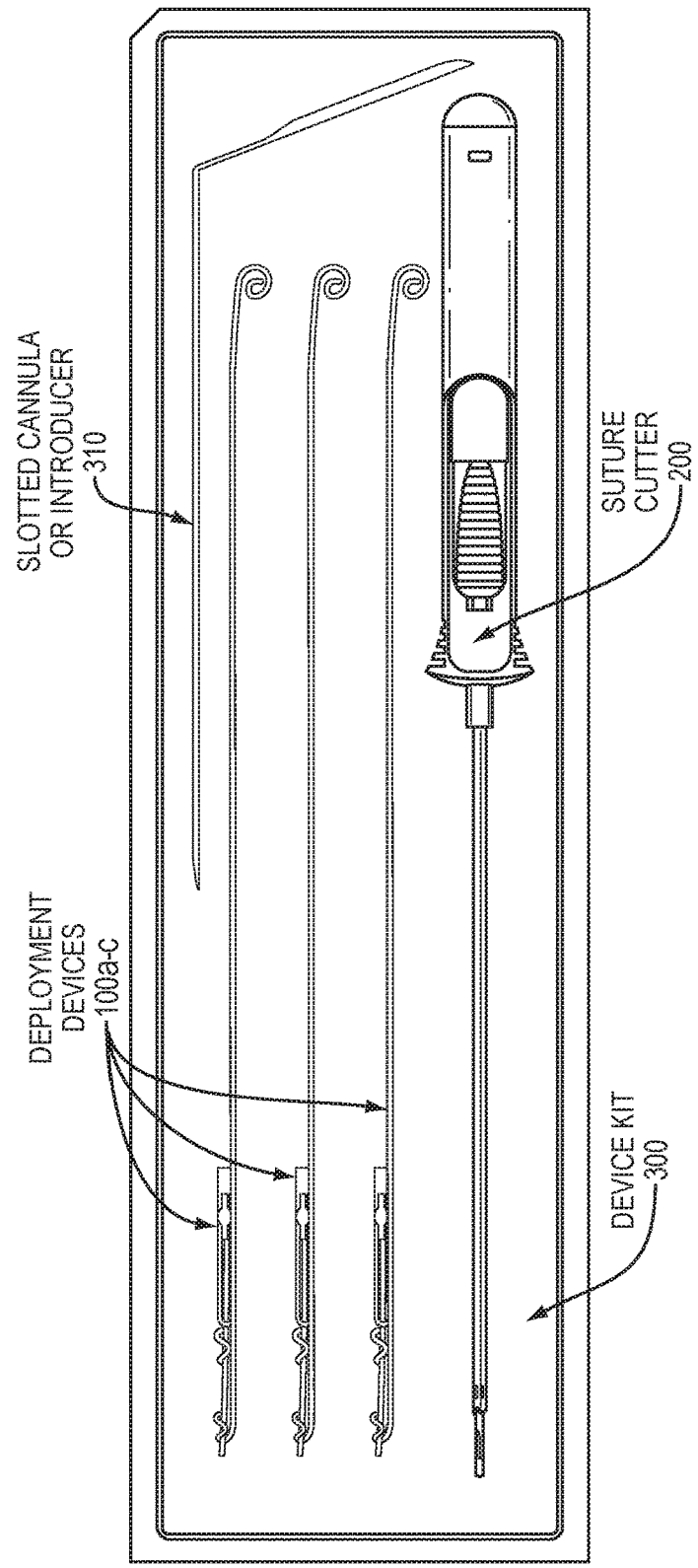

MODULAR TISSUE REPAIR KIT AND DEVICES AND METHOD RELATED THERETO

FIELD OF INVENTION

The present invention relates to a modular tissue repair kit, more particularly to a tissue repair kit including a modular implant/anchor deployment device that is coupled to another surgical device, and even more particularly to such a modular implant/anchor deployment device that is removably attached to a suture cutter from which combination implants are deployed. The present invention also features surgical methods that utilize such a modular tissue repair kit and modular implant/anchor deployment device and more particularly features surgical methods for use in repairing a damaged meniscus.

BACKGROUND OF THE INVENTION

The best outcomes for meniscal repair come from establishing the correct reduction of the torn tissue. In an arthroscopic procedure, the meniscus is often difficult to access and more difficult to repair. This is the case because of the risk of neurovascular injury. Presently, the methods that represent the gold standard of repair are sutured based. Methods having the cheapest cost involve a suture that is shuttled using long needles and cannulas as guides. Such a method involve making two incisions, one anterior and one posterior to the direction of the needle. It should be noted that such a method is not without risk of neurovascular injury. In addition, such methods also require the tying of knots arthroscopically and thereafter cutting of the suture, also arthroscopically. Another technique involves the use of a hybrid in which sutures are shuttled through spinal needles. While such methods are relatively inexpensive from the standpoint of the cost of materials and devices being used, these methods are necessarily labor intensive.

A number of products also have been developed, in which the suture is configured with pre-tied knots or the product includes the use of staples and tacks. A number of the suture based techniques also involve the use of an implant or suture anchor that is coupled to the suture. As is known in the art, the combined implant and suture are used to repair the damaged meniscus.

More particularly, a unique surgical device or surgical instrument is typically provided that is specifically configured and/or designed to deploy the implants or suture anchors for a meniscal or other tissue repair. Such a device/instrument includes a handle and a tubular assembly extending from the handle having a sharp distal end for insertion into the tissue. The tubular assembly is further configured so that one or two implants or the like that are connected to a suture(s), are slidably disposed in the tubular assembly. The surgeon uses the handle to manipulate the device to insert the sharp distal end into and through the tissue (e.g., meniscus). After such insertion, each implant is either passively or actively deployed. In passive deployment, the implant is withdrawn from the tubular assembly as the implant interacts with the tissue during a withdrawal motion of the device. In active deployment, the surgeon takes some action (e.g., pushes on a slide) that applies a force to the implant so it is pushed out of the tubular assembly.

If the device includes a second implant, the device is manipulated so as to cause the second implant to move from its storage position to the pre-deployment location in the tubular assembly. The device is again inserted into the tissue but most likely to a different tissue location and the second implant is deployed. The surgeon then takes the appropriate actions to tighten the suture and also to remove the device that was used to deploy the implants. After securing the implants and tightening the suture, the surgeon typically inserts a suture cutting device to cut the suture and typically remove the excess length of suture. As these sutures are pre-tied, the sutures are arranged so that when the surgeon applies a longitudinal force to the suture this shortens the suture and tightens the knot.

The tubular assembly also is typically provided in different configurations (e.g., straight distal end, curved or offset distal end) to facilitate implant deployment at different tissue locations. This means that a unique device is built for each configuration or different tubular assemblies are constructed for each configuration and these are separately mounted to a handle or handle assembly.

There is found in U.S. Publication No. 2013/0053884, a closure system for closing openings in tissue, where such a system includes a closure device and a fastener. Such a closure device also includes shafts that are configured to deploy the fastener to close the opening in the tissue. Such a closure device also includes shafts that are configured to deploy the fastener 500 to close the opening in the tissue. The fastener includes an opening that is formed therein and the sutures are received or drawn through the opening. Also, the closure device includes an outer shaft and an actuator (inner) shaft that are configured to deploy the fastener as either a knot replacement or a knot pusher. Further, the closure device is configured to trim the sutures after deployment. More particularly, the closure device includes cutters formed or included in the outer and actuator shafts that are configured to trim the sutures by relative movement of the outer and actuator shafts.

There is found in U. S. Publication No. 2004/0002734, which corresponds to U.S. Pat. No. 6,972,027, a suture anchor delivery system including a handle and a needle extending therefrom. Such a suture anchor delivery system also includes a suture anchor assembly that is slidably received on the needle. In a particular embodiment such a suture delivery system includes an insertion device and a suture anchor assembly disposed thereon. The suture delivery system also is configured for inserting suture anchors of the suture anchor assembly into soft tissue so as to subsequently facilitate repair of the soft tissue, such as the meniscus, tendons, ligaments, muscles, or the like. In the loaded state, the suture anchors are mounted on the needle.

There is found in U. S. Publication No. 2008/0091219, which corresponds to U.S. Pat. No. 7,918,868, an apparatus for suturing tissue, wherein the apparatus includes: a housing; a first needle mounted to the housing; a second needle mounted to the housing; a suture having a leading portion and a trailing portion; a first structure associated with the first needle for passing the leading portion of the suture from a near side of the tissue to a far side of the tissue; and a second structure associated with the second needle for retracting the leading portion of the suture from the far side of the tissue back to the near side of the tissue. Also included is a pre-formed, un-cinched knot formed in the trailing portion of the suture; and a support for releasably supporting the pre-formed, un-cinched knot relative to the housing.

Also found is a method for suturing tissue, the method including: providing a suture having a leading portion and a trailing portion, wherein a pre-formed, un-cinched knot is formed in the trailing portion of the suture; passing the leading portion of the suture from a near side of the tissue to a far side of the tissue; retracting the leading portion of the suture from the far side of the tissue back to the near side of the tissue; passing the retracted leading portion of the suture through the pre-formed, un-cinched knot formed in the trailing portion of the suture; and cinching the knot so as to secure the suture in the tissue.

There is found in U. S. Publication No. 2006/0009765, which corresponds to U.S. Pat. No. 7,632,284, an instrument kit for performing a repair on a meniscal tear. Such a kit includes at least one instrument or template that can be inserted within the knee area along a path adjacent to the tear and used to at least partially repair the meniscal tear. The instrument kit also can include a handle adapted to be removable attached to a proximal end of the template. The instrument kit for performing a repair procedure on a meniscal tear in a knee is used in combination with a meniscal repair device.

Such an instrument kit includes at least one template having an elongate body defining X, Y and Z axes. Preferably, the elongate body is adapted for insertion in a knee of the patient to approximate a path to a meniscal tear. The elongate body has a length along the X-axis sufficient to access the meniscal tear and a reduced profile to facilitate passage thereto. Upon subsequent removal of the template from the knee, a correspondingly dimensioned meniscal repair device is introduced along the path to the meniscal tear for repair using the opening formed by the template.

Such an instrument kit may further include a handle that is configured and adapted to be removably attached to a proximal end of each of the at least one template. Alternatively, the handle can be either integrally formed with or fixedly secured to a proximal end of the at least one template. Also found is a method of performing a repair procedure or a meniscal repair in a knee. Such a method includes introducing a selected elongate template within the knee area of a patient to approximate a path to a meniscal tear within the knee (e.g., grossly defines a path through the knee to the target site).

There is found in U. S. Publication No. 201110160767, which corresponds to U.S. Pat. No. 8,337,525, a fibrous tissue repair device including first and second tubular anchors having corresponding longitudinal passages and corresponding first and second inserters. Each inserter has a shaft with a distal portion received in the longitudinal passage of the corresponding tubular anchor. A flexible strand couples the first and second anchors. Also found is a kit for repairing soft tissue which may be used for meniscus repairs. While the description and drawing figures are illustrated in an application for meniscus repair in knee surgery, it also is provided that the teachings also can be used for repairing any fibrous tissue, such as muscle, ligament or tendon in an arthroscopic or other open procedure, including rotator cuff reconstruction, acromioclavicular (AC) reconstruction, anterior cruciate ligament reconstruction (ACL) and generally for fastening tendons, grafts, or strands to fibrous tissue and bone.

There is found in U. S. Publication No. 2009/0228041, an arthroscopic meniscal tear repair device including a catch needle and a transfer needle, which are both pierced into a torn meniscus and advanced past the tear. A suture is transferred by a suture needle from the transfer needle through the meniscus and into the catch needle. The catch needle has an internal mechanism that retains the suture. The suture needle is then retracted back to its home position inside the transfer needle, leaving the free end of the suture across the meniscus and in the catch needle. The device is then retracted out of the meniscus, leaving behind a stitch across the meniscal tear inside the meniscus. A pre-tied knot of suture is then slid down the device and cinched up using a knot pusher having a dilation tip, thus completing the repair. Also found is a system for repairing meniscal tear which may include sliding a pre-tied knot suture with a pusher. The pusher may be kitted with the device as a separate component. It also is provided that the geometry of the knot pusher, in particular, is unique relative to other minimally invasive surgical knot pushers because of the dilation tip.

As indicated in above discussion, each of the above described systems, methods and devices utilize a uniquely constructed suture anchor delivery device to localize a suture anchor with respect to the targeted area and then deliver the suture anchor to the targeted area. This necessarily increases the part count associated with any kit as well as requiring the controlled manufacture and storage of such devices.

It thus would be desirable to provide an implant deployment/delivery module/device that is adaptable for use with another surgical device such as a suture cutter and which can utilize functionalities of such another surgical device or suture cutter in the process of localizing the implant/anchor with respect to the targeted area device as well as delivering or deploying the implant/anchor to the targeted area. Such an implant deployment device/module preferably does not increase the level of difficulty to the users as compared to methods embodying the use of conventional delivery/deployment devices. Such an implant deployment/delivery module/device also preferably should not be more costly that the conventional devices.

SUMMARY OF THE INVENTION

In its broadest aspects, the present invention features a modular kit concept in which an implant deployment device/module is configured and arranged to hold the implants/anchors for deployment and where the module is further configured and arranged so it can be removably secured to a conventional surgical device (e.g., a suture cutter) that also could be separately used during the surgical procedure. Functionalities of the conventional surgical device are used in combination with the implant deployment device/module to insert the device/module as well as each implant/anchor into the tissue and to deploy each implant/anchor either passively or actively.

In particular embodiments the conventional surgical device is a suture cutter as is known to those skilled in the art. For example, the suture cutter could be that associated with the Smith & Nephew FastFix Suture System or other such suture systems that are known in the art (e.g., Smith & Nephew Fast-Fix 360 Meniscal Repair System).

More particularly, the present invention features an implant/anchor deployment device/module, a modular kit concept embodying such an implant/anchor deployment device/module, a system for deploying an implant/anchor into tissue, and a method for treating damaged tissue using such an implant/anchor such as for example, a method for deploying one or more anchors/implants during a meniscal repair procedure. In yet further aspects/embodiments of the present invention, the implant/anchor deployment device/module is operably coupled to a surgical device whose functionalities are utilized to cause the deployment of an anchor/implant from the implant/anchor deployment device/module.

More particularly, such an implant deployment device/module is configured and arranged to hold the implants/anchors for deployment and the module is further configured and arranged so it can be removably secured to a conventional surgical device (e.g., a suture cutter) that also could be used during the surgical procedure after it has been decoupled from the implant deployment device/module. Functionalities of the conventional surgical device are used in combination with the implant deployment device/module to cause each implant to be inserted into the tissue and to deploy each implant/anchor either passively or actively. In particular embodiments the conventional surgical device is a suture cutter as is known to those skilled in the art. For example, the suture cutter could be that associated with the Smith & Nephew FastFix Suture System or other such suture systems that are known in the art (e.g., Smith & Nephew Fast-Fix 360 Meniscal Repair System). In addition, such an implant/anchor can include a suture anchor such as those known to those skilled in the art.

According to one aspect of the present invention, there is featured a modular implant/anchor deployment device for use with a surgical device. Such a deployment device includes a body member having a proximal end portion and a distal end portion, the distal end portion being configured so that an implant/anchor can be deployed therefrom. Also, the proximal end portion is configured so as to be removably attached to a first end portion of the surgical device. In further aspects/embodiments, the proximal end portion of the body member is further configured so as to include an enlarged portion for receiving therein the first end portion of the surgical device.

In yet further aspects/embodiments, the surgical device includes a first member that includes the first end portion of the surgical device. Additionally, the body member proximal end portion is further configured so as to be removably attached to opposing structure of the first member of the surgical device including the first end portion. In further aspects/embodiments, the body member proximal end portion is further configured so as to include a connector, mechanism or structure that is configured so as to removable engage a complimentary feature, mechanism, sub-structure or the like provided in the opposing structure of the first member. In more particular aspects/embodiments, the complimentary feature includes an opening, artifact (e.g., surface artifact), depressed region or depression, aperture or the like that is provided in the surgical device (e.g., suture cutter), either for the device's intended function or for purposes of engaging with the anchor deployment device.

The connector, mechanism or structure removably engaging the complimentary feature, forms a securing mechanism, structure or connector that is secured, coupled, attached or integrally formed with the body member proximal end portion and which is arranged so that a portion of the securing mechanism removably engages the complementary feature of the inner member.

In exemplary embodiments, the securing mechanism forms a latching type of mechanism that latches to or removably engages the surgical device distal end or suture cutter inner member so as to restrain axial movement in the direction of withdrawal. More particularly, the securing mechanism includes a cantilevered structure that is coupled, attached or otherwise formed integral with the body member proximal end portion. Such a cantilevered structure also includes a protrusion or prong like element that extends outwardly therefrom and into the lumen to engage the complimentary feature.

In further aspects/embodiments, the securing mechanism also includes a manipulating portion that is configured to allow a surgeon to manipulate the cantilevered structure so the protrusion can be disengaged from the complimentary feature. For example, the manipulating portion can be configured and arranged so as to allow the surgeon to move the prong or protrusion in an outwardly direction out of engagement with the complimentary feature thereby allowing the surgical device to be detached or decoupled from the deployment device.

In yet further aspects/embodiments, the surgical device includes a second member having a lumen extending along the long axis. Additionally, the surgical device first member is disposed within the second member lumen and the first and second members are movable with respect to each other. In more particular aspects/embodiments, the second member is movable along the long axis with respect to the first member.

In yet further aspects/embodiments, such a modular implant/anchor deployment device further includes one or more implants/anchors that are movably disposed on the body member proximal end portion. Additionally, movement of the second member along the long axis in one direction moves each of the at least one implants/anchors to a pre-deployment position.

In yet further aspects/embodiments, such a modular implant/anchor deployment device further includes a plurality of implants/anchors that are movably disposed on the body member distal end portion and movement of the second member along the long axis in the one direction causes the second implant/anchor to be moved to a pre-deployment position after deployment of the first implant/anchor.

In yet further aspects/embodiments, a tip of the body member distal end portion is configured for insertion into tissue.

In yet more particular aspects/embodiments, the surgical device is a suture cutter having a movable outer member and an inner member, where the inner member is removably attached to the body member proximal end portion.

In yet more particular aspects/embodiments, the body member includes a lumen extending along the long axis in at least the distal end portion and a slotted opening in communication with the lumen also extending along the long axis. As indicated herein, in yet further aspects/embodiments, such a modular implant/anchor deployment device further includes one or more implants/anchors that are movably disposed on the body member distal end portion. More particularly, each of the at least one implant/anchor is movably disposed in the slotted opening such that a portion of the implant/anchor extends above an outer surface of the body member distal portion. In yet more particular embodiments, the movement of the second member along the long axis in one direction moves each of the at least one implants/anchors to a pre-deployment position (e.g., from a stored, initial or intermediate position to a pre-deployment position).

In yet further aspects/embodiments, each of the at least one implant/anchor or each of a plurality of such implants/anchors are configured and arranged so that each of the implants/anchors are coupled to each other by a suture.

In yet further aspects/embodiments, the body member distal end portion is configured and arranged so as to have a given profile in an X-Y-Z direction. In further aspects/embodiments, the given profile is such that a long axis of the body member distal end portion parallels a long axis of the surgical device first member or the given profile is such that a long axis of the body member distal end portion is at an angle with respect to a long axis of the surgical device first member. In yet further aspects the long axis of the distal end portion is arcuate or curved and so the curved segment or portion lies in a single plane or is such as to form a 3-dimensional structure.

In yet further aspects/embodiments, the distal end portion of the body member is further configured so as to have a given geometry selected for facilitating navigation of the distal end portion to the targeted area. In more particular aspects, where the invention can include a plurality of such modular implant/anchor deployment devices, the geometry of at least one body member distal end portion is different from the geometry of another body member distal end portion.

According to yet another aspect of the present invention, there is featured another implant deployment device/module that can deliver or deploy an implant such as a suture anchor, into tissue. Such an implant deployment device/module includes an implant holding member that holds one or more implant for deployment; the implant holding member having a first end and a second end. The holding member first end is configured so as to be inserted into tissue and so that the one or more implants can be deployed therefrom. The holding member second end is configured so as to be removably secured to an end portion of a surgical device. When the holding member second end is removably secured to the surgical device end portion a functionality of the surgical device is operably coupled to the holding member second end.

In yet further aspects/embodiments, the holding member second end also is configured so as to include a connector, mechanism or structure that is configured so as to removable engage a complimentary feature, mechanism, sub-structure or the like provided in the surgical device end portion. In this way, when the mechanism or the like and the complimentary feature or the like are respectively positioned, the mechanism removably engages the complimentary feature and the implant holding member is not movable axially with respect to the surgical device.

In further aspects/embodiments, the holding member proximal end portion is further configured so as to include the connector, mechanism or structure. In more particular aspects/embodiments, the complimentary feature includes an opening, artifact (e.g., surface artifact), depressed region or depression, aperture or the like that is provided in the surgical device (e.g., suture cutter), either for the device's intended function or for purposes of engaging with the anchor deployment device.

The connector, mechanism or structure removably engaging the complimentary feature, forms a securing mechanism, structure or connector that is secured, coupled, attached or integrally formed with the holding member proximal end portion and which is arranged so that a portion of the securing mechanism removably engages the complimentary feature of the inner member.

In exemplary embodiments, the securing mechanism forms a latching type of mechanism that latches to or removably engages the surgical device distal end or suture cutter inner member so as to restrain axial movement in the direction of withdrawal. More particularly, the securing mechanism includes a cantilevered structure that is coupled, attached or otherwise formed integral with the holding member proximal end portion. Such a cantilevered structure also includes a protrusion or prong like element that extends outwardly therefrom and into the lumen to engage the complimentary feature.

In further aspects/embodiments, the securing mechanism also includes a manipulating portion that is configured to allow a surgeon to manipulate the cantilevered structure so the protrusion can be disengaged from the complimentary feature. For example, the manipulating portion can be configured and arranged so as to allow the surgeon to move the prong or protrusion in an outwardly direction out of engagement with the complimentary feature thereby allowing the surgical device to be detached or decoupled from the deployment device.

In yet further aspects/embodiments, the holding member first end is configured so as to have a given profile in an X-Y-Z direction. In further aspects/embodiments, the given profile is such that a long axis of the holding member second end corresponds to a long axis of the holding member first end, or the given profile is such that a long axis of the holding member second end is at an angle with respect to a long axis of the holding member first end. In yet further aspects/embodiments, the distal end portion or holding member second end is configured and arranged so as to have an arcuate or curved profile that is arranged so the curved segment or portion lies in a single plane or is such as to form a 3-dimensional structure.

In yet further aspects/embodiments, the implant deployment device/module is used in combination with the surgical device. Also, the surgical device can be a suture cutter.

While in an illustrated embodiment, the surgical device second member is movable with respect to the surgical device first member this shall not be limiting as to the scope of the present invention. It is contemplated and thus within the scope of the present invention for the first member to be movable with respect to the second member. Additionally, it is contemplated that the body member proximal end can be secured to the first end portion of the surgical device and for the first member to move within a lumen of the body member so as to cause each implant anchor to move along the long axis to a pre-deployment position.

According to yet another aspect of the present invention there is featured a system for deploying an implant/anchor in tissue. Such a system includes a surgical device that is configured to perform a procedure not directly related to deployment of an implant/anchor and a modular implant/anchor deployment device such as that described herein. In more particular embodiments, such a system includes at least one modular implant/anchor deployment device, one or more modular implant/anchor deployment devices, a plurality of such modular implant/anchor deployment devices or a multiplicity (e.g., 3-6 or more) of such modular implant/anchor deployment devices.

In particular aspects/embodiments, each of such modular implant/anchor deployment devices includes a body member having a proximal end portion and a distal end portion, the distal end portion being configured so that an implant/anchor can be deployed therefrom. Also, the proximal end portion is configured so as to be removably attached to a first end portion of the surgical device. In further aspects/embodiments, the proximal end portion of the body member is further configured so as to include an enlarged portion for receiving therein the first end portion of the surgical device.

In yet further aspects/embodiments, the surgical device includes a first member that includes the first end portion of the surgical device. Additionally, the body member proximal end portion is further configured so as to be removably attached to opposing structure of the first member of the surgical device including the first end portion. In further aspects/embodiments, the body member proximal end portion is further configured so as to include a connector, mechanism or structure that is configured so as to removable engage a complimentary feature, mechanism, sub-structure or the like provided in the opposing structure of the first member. In more particular aspects/embodiments, the complimentary feature includes an opening, artifact (e.g., surface artifact), depressed region or depression, aperture or the like that is provided in the surgical device (e.g., suture cutter), either for the device's intended function or for purposes of engaging with the anchor deployment device.

The connector, mechanism or structure removably engaging the complimentary feature, forms a securing mechanism, structure or connector that is secured, coupled, attached or integrally formed with the body member proximal end portion and which is arranged so that a portion of the securing mechanism removably engages the complementary feature of the inner member.

In exemplary embodiments, the securing mechanism forms a latching type of mechanism that latches to or removably engages the surgical device distal end or suture cutter inner member so as to restrain axial movement in the direction of withdrawal. More particularly, the securing mechanism includes a cantilevered structure that is coupled, attached or otherwise formed integral with the body member proximal end portion. Such a cantilevered structure also includes a protrusion or prong like element that extends outwardly therefrom and into the lumen to engage the complimentary feature.

In further aspects/embodiments, the securing mechanism also includes a manipulating portion that is configured to allow a surgeon to manipulate the cantilevered structure so the protrusion can be disengaged from the complimentary feature. For example, the manipulating portion can be configured and arranged so as to allow the surgeon to move the prong or protrusion in an outwardly direction out of engagement with the complimentary feature thereby allowing the surgical device to be detached or decoupled from the deployment device.

In yet further aspects/embodiments, the surgical device includes a second member having a lumen extending along the long axis. Additionally, the surgical device first member is disposed within the second member lumen and the first and second members are movable with respect to each other. In more particular aspects/embodiments, the second member is movable along the long axis with respect to the first member.

In yet further aspects/embodiments, such a modular implant/anchor deployment device further includes one or more implants/anchors that are movably disposed on the body member distal end portion. Additionally, movement of the surgical device second member along the long axis in one direction moves each of the at least one implants/anchors from a stored, initial or intermediate position to a pre-deployment position.

In yet further aspects/embodiments, such a modular implant/anchor deployment device further includes a plurality of implants/anchors that are movably disposed on the body member distal end portion and movement of the surgical device second member along the long axis in the one direction causes the second implant/anchor to be moved to a pre-deployment position after deployment of the first implant/anchor.

In yet further aspects/embodiments, a tip of the body member distal end portion is configured for insertion into tissue.

In yet more particular aspects/embodiments, the surgical device is a suture cutter having a movable outer member and an inner member, where the inner member is removably attached to the body member proximal end portion.

In yet more particular aspects/embodiments, the body member includes a lumen extending along the long axis in at least the distal end portion and a slotted opening in communication with the lumen also extending along the long axis. As indicated herein, in yet further aspects/embodiments, such a modular implant/anchor deployment device further includes one or more implants/anchors that are movably disposed on the body member distal end portion. More particularly, each of the at least one implant/anchor is movably disposed in the slotted opening such that a portion of each implant/anchor extends above an outer surface of the body member distal portion. In yet more particular embodiments, the movement of the surgical device second member along the long axis in one direction moves each of the at least one implants/anchors to a pre-deployment position (e.g., from a stored, initial or intermediate position to a pre-deployment position).

In yet further aspects/embodiments, each of the at least one implant/anchor or each of a plurality or multiplicity of such implants/anchors are configured and arranged so that each of the implants/anchors are coupled to each other by a suture.

In yet further aspects/embodiments, the body member distal end portion is configured and arranged so as to have a given profile in an X-Y-Z direction. In further aspects/embodiments, the given profile is such that a long axis of the body member distal end portion parallels a long axis of the surgical device first member or the given profile is such that a long axis of the body member distal end portion is at an angle with respect to a long axis of the surgical device first member. In yet further aspects/embodiments, the distal end portion is configured and arranged so as to have an arcuate or curved profile that is arranged so that the curved portion lies in a single plane or is such as to form a 3-dimentional curved structure.

In yet further aspects/embodiments, the distal end portion of the body member is further configured so as to have a given geometry that is selected for facilitating the navigation of the distal end portion to the targeted tissue area. In more particular aspects, where the invention can include a plurality of such modular implant/anchor deployment devices, the geometry of at least one body member distal end portion is different from the geometry of another body member distal end portion.

According to yet another aspect of the present invention, there is featured a method for treating damaged tissue using such a deployed implant/anchor. In more particular aspects/embodiments there is featured a method for deploying one or more anchors/implants during a tissue repair procedure such as a repair procedure for repairing a damaged meniscus.

Such methods include providing at least one modular implant/anchor deployment device and a surgical device configured to perform a procedure not directly related to deployment of an implant/anchor. The provided at least one modular implant/anchor deployment device also includes a body member having a proximal end portion and a distal end portion, the distal end portion being configured so that an implant/anchor can be deployed therefrom. Further, the proximal end portion is configured so as to be removably attached to a first end portion of the surgical device.

Such methods further include removably securing the body member proximal end portion to the first end portion of the surgical device as well as inserting the modular implant/anchor deployment device and at least the coupled portion of the surgical device into a body of a patient. Additionally, such methods further include locating the body member distal end portion at a desired location within the body and deploying the implant/anchor from the body member distal end portion. In yet further aspects/embodiments, such locating includes manipulating the coupled surgical device so that the distal end portion is so located at the desired body location. In further aspects/embodiments, the proximal end portion of the body member is further configured so as to include an enlarged portion for receiving therein the first end portion of the surgical device.

In further aspects/embodiments, such methods further include manipulating the surgical device, after locating the body member distal end portion, so that the distal end portion passes through the meniscus. Also, such deploying includes deploying the implant/anchor after such manipulating. Further, after completing deploying the implant/anchor such methods further include de-connecting the body member proximal end portion from the first end portion of the surgical device, thereby allowing the surgical device to be thereafter used in the intended manner. In more specific embodiments, after such deploying, such methods include withdrawing the coupled deployment device and surgical device from the body before performing such de-connecting.

In further aspects/embodiments, the body member proximal end portion is further configured so as to include a connector, mechanism or structure that is configured so as to removably engage a complimentary feature, mechanism, sub-structure or the like provided in the opposing structure of the surgical device first member. In more particular aspects/embodiments, the complimentary feature includes an opening, artifact (e.g., surface artifact), depressed region or depression, aperture or the like that is provided in the surgical device (e.g., suture cutter), either for the device's intended function or for purposes of engaging with the anchor deployment device. Such removably securing the body member proximal end portion to the first end portion of the surgical device also further includes removably engaging the body member a connector, mechanism or structure with the surgical device complimentary feature or the like. More specifically removably engaging the protrusion with the aperture.

The connector, mechanism or structure removably engaging the complimentary feature, forms a securing mechanism, structure or connector that is secured, coupled, attached or integrally formed with the body member proximal end portion and which is arranged so that a portion of the securing mechanism removably engages the complementary feature of the inner member.

In exemplary embodiments, the securing mechanism forms a latching type of mechanism that latches to or removably engages the surgical device distal end or suture cutter inner member so as to restrain axial movement in the direction of withdrawal. More particularly, the securing mechanism includes a cantilevered structure that is coupled, attached or otherwise formed integral with the body member proximal end portion. Such a cantilevered structure also includes a protrusion or prong like element that extends outwardly therefrom and into the lumen to engage the complimentary feature.

In further aspects/embodiments, the securing mechanism also includes a manipulating portion that is configured to allow a surgeon to manipulate the cantilevered structure so the protrusion can be disengaged from the complimentary feature. For example, the manipulating portion can be configured and arranged so as to allow the surgeon to move the prong or protrusion in an outwardly direction out of engagement with the complimentary feature thereby allowing the surgical device to be detached or decoupled from the deployment device.

In yet further aspects/embodiments, the provided surgical device includes a first member including the first end portion of the surgical device and the body member proximal end portion is further configured so as to be removably attached to opposing structure of the first member of the surgical device including the first end portion. Additionally, such removably securing includes removably securing the body member proximal end portion to the opposing structure of the first member.

In yet further aspects/embodiments, the provided surgical device is a suture cutter having a movable outer member and an inner member, where the inner member is removably attached to the body member proximal end portion.

In yet further aspects/embodiments, the provided surgical device includes a second member having a lumen extending along the long axis, where the surgical device first member is disposed within the second member lumen and the first and second members are movable with respect to each other. In more particular aspects/embodiments, the second member is movable along the long axis with respect to the first member.

In yet further aspects/embodiments, the provided modular implant/anchor deployment device further includes one or more implants/anchors that are movably disposed on the body member distal end portion. Additionally, such methods further include moving the surgical device second member along the long axis in one direction so as to move each of the at least one implants/anchors to a pre-deployment position (e.g., from a stored, initial or intermediate position).

In yet further aspects/embodiments, the provided modular implant/anchor deployment device further includes a plurality or a multiplicity of implants/anchors. Also such movement of the surgical device second member along the long axis in the one direction also can cause the second implant/anchor to be moved to a pre-deployment position after deployment of the first implant/anchor.

In yet more particular aspects/embodiments, the body member includes a lumen extending along the long axis in at least the distal end portion and a slotted opening in communication with the lumen also extending along the long axis. As indicated herein, in yet further aspects/embodiments, such a modular implant/anchor deployment device further includes one or more implants/anchors that are movably disposed on the body member proximal end portion. More particularly, each of the at least one implant/anchor is movably disposed in the slotted opening such that a portion of the implant/anchor extends above an outer surface of the body member distal portion.

In yet more particular embodiments, the movement of the surgical device second member along the long axis in one direction moves each of the at least one implants/anchors to a pre-deployment position (e.g., from a stored, initial or intermediate position to a pre-deployment position). Additionally, such methods further include moving the second member along the long axis in the "one direction" so as to thereby move each of the implants/anchors within the slotted opening to a pre-deployment position.

In yet further aspects/embodiments, each of the at least one implant/anchor or each of a plurality or multiplicity of such implants/anchors are configured and arranged so that each of the implants/anchors are coupled to each other by a suture(s). Further, such methods include manipulating the suture(s) following deployment of the at least one implant/anchor or the plurality or multiplicity of such implants/anchors so as to draw the damaged tissue into engagement.

In yet further aspects/embodiments, where the surgical device is a suture cutter, such methods further include de-connecting the coupled suture cutter from the modular implant/anchor deployment device and thereafter using the de-coupled suture cutter to cut the suture (e.g., excess length of suture).

In yet further aspects/embodiments, the body member distal end portion is configured and arranged so as to have a given profile in an X-Y-Z direction. In more particular aspects/embodiments, the given profile is such that a long axis of the body member distal end portion parallels a long axis of the surgical device first member or the given profile is such that a long axis of the body member distal end portion is at an angle with respect to a long axis of the surgical device first member. In yet further aspects/embodiments, the distal end portion is configured and arranged so as to have an arcuate or curved profile that is arranged so the curved portion lies in a single plane or is such as to form a 3-dimentional structure.

In yet further aspects/embodiments, the distal end portion of the body member is configurable so as to have a given geometry that is established to facilitate the navigation of the distal end portion to the targeted tissue area. In more particular aspects, where the invention can include a plurality or multiplicity (e.g., 3-6 or more) of such modular implant/anchor deployment devices, the geometry of at least one body member distal end portion is different from the geometry of another body member distal end portion.

In further aspects/embodiments, such methods include selecting a given modular implant/anchor deployment device having a desired profile or geometry and wherein such locating of the body member distal end portion includes manipulating the selected modular implant/anchor deployment device so that the body member distal end portion having the desired profile or geometry is located proximal the targeted tissue area or repair site.

In yet further aspects/embodiments, such methods further include passing at least a segment of the distal end portion through the tissue or meniscus and thereafter deploying an implant/anchor. Thereafter such methods further include withdrawing the distal end portion from the tissue and if there is another implant/anchor to be deployed locating the distal end portion at another location and repeating the process for deploying the another implant/anchor.

According to still yet another aspect of the present invention, there is featured a surgical device kit. Such a surgical device kit includes a surgical device that is configured to perform a procedure not directly related to deployment of an implant/anchor and at least one modular implant/anchor deployment device. In further aspects/embodiments, the surgical device is a suture cutter.

Each of the at least one modular implant/anchor deployment device includes a body member having a proximal end portion and a distal end portion. The distal end portion is configured so that an implant/anchor can be deployed therefrom. The proximal end portion is configured so as to be removably attached to a first end portion of the surgical device.

In further aspects/embodiments, the proximal end portion of the body member is further configured so as to include one or both of an enlarged portion for receiving therein the first end portion of the surgical device and a connector, mechanism or structure that is configured so as to removably engage a complimentary feature, mechanism, sub-structure or the like provided in the opposing structure of the surgical device first member. In more particular aspects/embodiments, the complimentary feature includes an opening, artifact (e.g., surface artifact), depressed region or depression, aperture or the like that is provided in the surgical device (e.g., suture cutter), either for the device's intended function or for purposes of engaging with the anchor deployment device. Such removably securing the body member proximal end portion to the first end portion of the surgical device also further includes removably engaging the body member a connector, mechanism or structure with the surgical device complimentary feature or the like. More specifically removably engaging the protrusion with the aperture.

The connector, mechanism or structure removably engaging the complimentary feature, forms a securing mechanism, structure or connector that is secured, coupled, attached or integrally formed with the body member proximal end portion and which is arranged so that a portion of the securing mechanism removably engages the complementary feature of the inner member.

In exemplary embodiments, the securing mechanism forms a latching type of mechanism that latches to or removably engages the surgical device distal end or suture cutter inner member so as to restrain axial movement in the direction of withdrawal. More particularly, the securing mechanism includes a cantilevered structure that is coupled, attached or otherwise formed integral with the body member proximal end portion. Such a cantilevered structure also includes a protrusion or prong like element that extends outwardly therefrom and into the lumen to engage the complimentary feature.

In further aspects/embodiments, the securing mechanism also includes a manipulating portion that is configured to allow a surgeon to manipulate the cantilevered structure so the protrusion can be disengaged from the complimentary feature. For example, the manipulating portion can be configured and arranged so as to allow the surgeon to move the prong or protrusion in an outwardly direction out of engagement with the complimentary feature thereby allowing the surgical device to be detached or decoupled from the deployment device.

In yet further aspects/embodiments, the provided surgical device includes a first member including the first end portion of the surgical device and the body member proximal end portion is further configured so as to be removably attached to opposing structure of the first member of the surgical device including the first end portion. Additionally, such removably securing includes removably securing the body member proximal end portion to the opposing structure of the first member.

In yet further aspects/embodiments, the distal end portion of the body member is further configured so as to have a given geometry selected for facilitating the navigation of the distal end portion to the targeted area.

In yet further aspects/embodiments, such a surgical kit further includes a plurality or multiplicity of such modular implant/anchor deployment devices, where the distal end portion of each body member is further configured so as to have a given geometry selected for facilitating the navigation of the distal end portion to the targeted area. Also, the geometry of at least one body member distal end portion of the kit is different from the geometry of another body member distal end portion of the kit.

In yet further aspects/embodiments, the suture cutter has a movable outer member and an inner member, where an end of the inner member is removably attached to the body member proximal end portion.

In yet further aspects/embodiments, the body member distal end portion is further configured so as to have a given geometry or profile established to facilitate the navigation of the distal end portion to the targeted area. For example, the distal end portion can present a straight geometry, a distal end that is formed at an angle with respect to the long axis of the body member or be arranged so as to present a curved or arcuate geometry. Such curving and angles can be established so as to be in one of two different directions, be in the same plane or different planes or form a 3 dimensional structure. In this way, a surgeon can be presented with a number of different modular implant/anchor deployment devices from which the surgeon can select the one which is best suited for performing a given tissue repair procedure.

In yet further aspects/embodiments such a surgical device kit can embody one or more, a plurality or a multiplicity of modular implant/anchor deployment devices as described herein.

Other aspects and embodiments of the invention are discussed below.

DEFINITIONS

The instant invention is most clearly understood with reference to the following definitions:

USP or USP No. shall be understood to mean U.S. Patent Number and U.S. Publication No. shall be understood to mean U.S. Published Patent Application Number.

The terms "comprising" and "including" as used in the discussion directed to the present invention and the claims are used in an open-ended fashion and thus should be interpreted to mean "including, but not limited to." Also the terms "couple" or "couples" is intended to mean either an indirect or direct connection. Thus if a first component is coupled to a second component, that connection may be through a direct connection, or through an indirect connection via other components, devices and connections. Further the terms "axial" and "axially" generally mean along or substantially parallel to a central or longitudinal axis, while the terms "radial" and "radially" generally mean perpendicular to a central, longitudinal axis.

Additionally directional terms such as "above," "below," "upper," "lower," etc. are used for convenience in referring to the accompanying drawing figures. In general, "above," "upper," "upward" and similar terms refer to a direction toward a proximal end of an instrument, device, apparatus or system and "below," "lower," "downward," and similar terms refer to a direction toward a distal end of an instrument, device, apparatus or system, but is meant for illustrative purposes only and the terms are not meant to limit the disclosure.

As used herein the terms "cutting" or "cut" when used in describing the methods, instruments or apparatus of the present invention shall be understood to be inclusive of any of a number of techniques or operations know in the art for surgically working bone, cartilage, ligaments or tissue such techniques include but are not limited to trimming, shaping, resecting, abrading or grinding of bone or tissue.

The term tissue when used hereinafter shall be understood to be parts or structure of a human body including, but not limited to skin, subcutaneous material, cartilage, muscle, bone, bony structures (e.g., vertebrae) and ligaments. More specifically, the term tissue shall be understood to particularly include or refer to parts or structure of a human body associated with the knee or knee joint.

BRIEF DESCRIPTION OF THE DRAWING

For a fuller understanding of the nature and desired objects of the present invention, reference is made to the following detailed description taken in conjunction with the accompanying drawing figures wherein like reference character denote corresponding parts throughout the several views and wherein:

FIG. 5 is an illustrative view showing an exemplary device kit that can include one or more suture anchor delivery devices according to the present invention.

DESCRIPTION OF THE PREFERRED EMBODIMENT

Figure 1A:
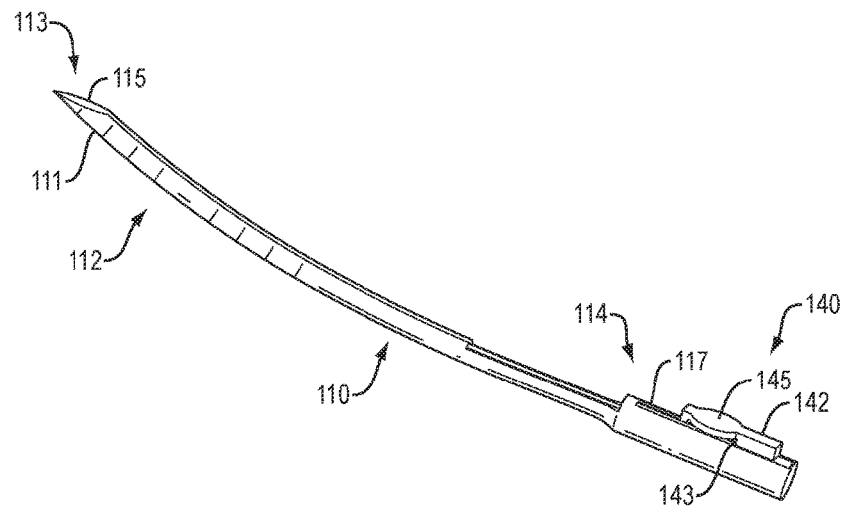
FIG. 1A is a perspective view of a modular suture anchor delivery device according to the present invention without the suture anchors.

The present invention features, devices, methods, systems and device kits all of which are useable in connection with treating or repairing damaged tissue such as tissue associated with the structure of a knee and more specifically, the tissue associated with repairing a damaged meniscus. More particularly, the present invention features an implant/anchor deployment device/module, a modular kit concept embodying one or more such implant/anchor deployment devices/modules, a system for deploying an implant/anchor into tissue, and a method for treating damaged tissue using such an implant/anchor such as for example, a method for deploying one or more anchors/implants during a meniscal repair procedure.

Such an implant/anchor deployment device/module, also is configured and arranged so it can be removably secured to a conventional surgical device (e.g., a suture cutter) that also could be used during the surgical procedure. Such a surgical device, however, is not of the type one usually associates with the deployment of such implants/anchors (e.g., suture anchors) into tissue. The functionalities of such a surgical device are used in combination with the implant/anchor deployment device/module so that each implant/anchor can be located with respect to a targeted tissue area within the body and so that the implant/anchor deployment device/module can be used to deploy each implant/anchor either passively or actively.

In particular embodiments the conventional surgical device is a suture cutter as is known to those skilled in the art. In more specific embodiments, the suture cutter is that associated with the Smith & Nephew FastFix Suture System or other such suture systems known in the art (e.g., Smith & Nephew Fast-Fix 360 Meniscal Repair System). While the design and functionalities of a suture cutter may be particularly suitable for use with the implant/anchor deployment device/module of the present invention, this shall not be considered as limiting the present invention to this specific surgical device as it is within the scope of the present invention for the implant/anchor deployment device/module to be used with other surgical devices which can be adapted for such use or for which the device/module can be adapted for use with functionalities of such other surgical devices.

Because of the modular concept embodied in the implant/anchor deployment device/module of the present invention, the surgical device can be used with any of a number of such implant/anchor deployment devices/modules so that any number of implants/anchors can be deployed at desired targeted tissue locations to treat the damaged tissue. Further, when the required number of implants/anchors have been deployed, the modularity embodied in the present invention also allows the surgeon or other surgical personnel to de-couple or de-connect the implant/anchor deployment device/module from the surgical device so that the surgeon can thereafter use the de-coupled surgical device in the intended manner. In other words, a unique device need not be made or manufactured solely for the purpose of delivering and deploying an implant/anchor to a targeted tissue location.

Also, while the implant/anchor deployment device/module can be coupled, secured or attached to the surgical device using any of a number of techniques known in the art, such coupling, attaching or securing does not affect the ability of the surgical device to perform its intended function after the implant/anchor deployment device/module is decoupled, detached or otherwise no longer secured to the surgical device. For example, when the surgical device is a suture cutter, the surgeon can decouple or detach the suture cutter from the implant/anchor deployment device/module and the surgeon can thereafter use the suture cutter to cut sutures such as the sutures which are coupled to the implants/anchors.

Figure 2A:
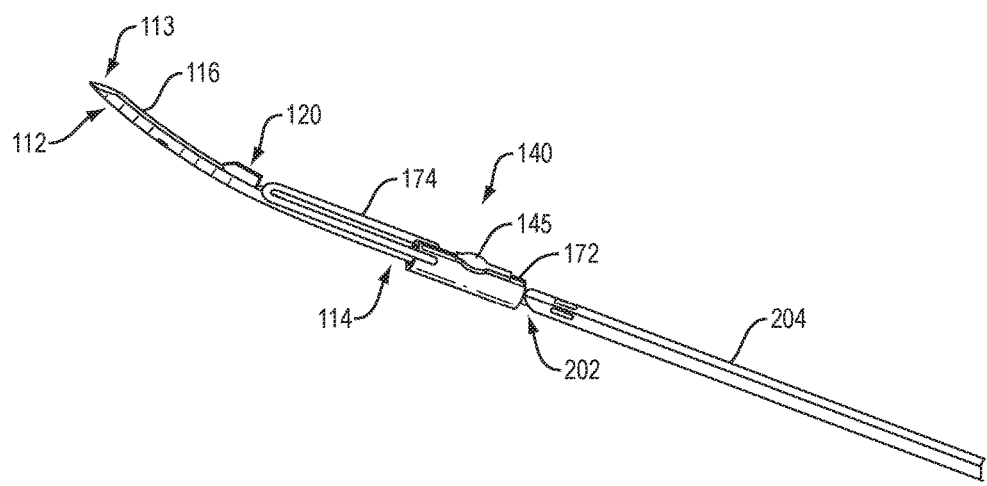
FIG. 2A is a perspective view of a modular suture anchor delivery device without suture anchors and functionalities of the surgical device.
Figure 2B:
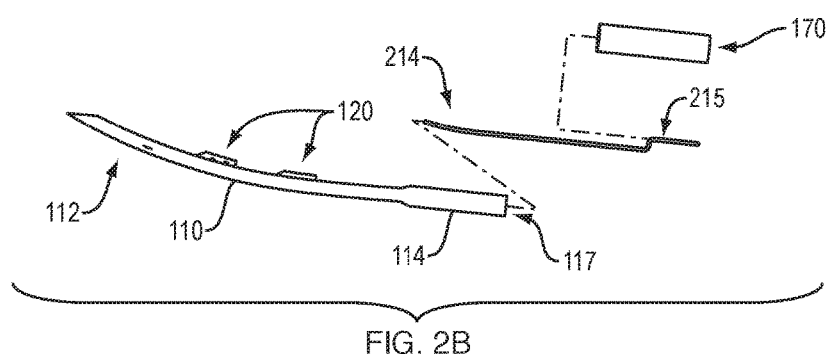
FIG. 2B is an exploded side view of a modular suture anchor delivery device and functionalities of the surgical device.
Figure 3:
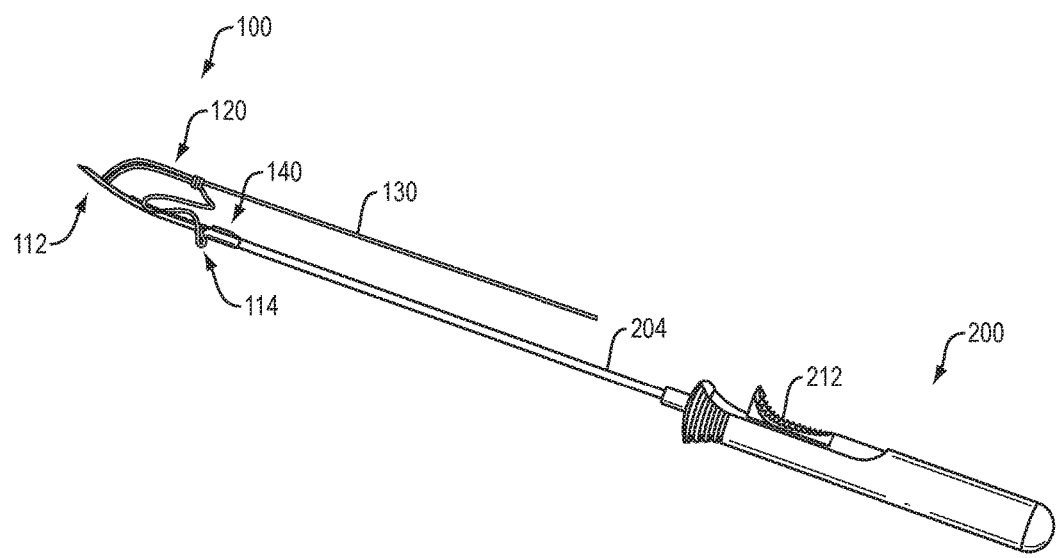
FIG. 3 is another perspective view of the modular suture anchor delivery device when coupled or attached to the end of the surgical device.
Figure 4A:
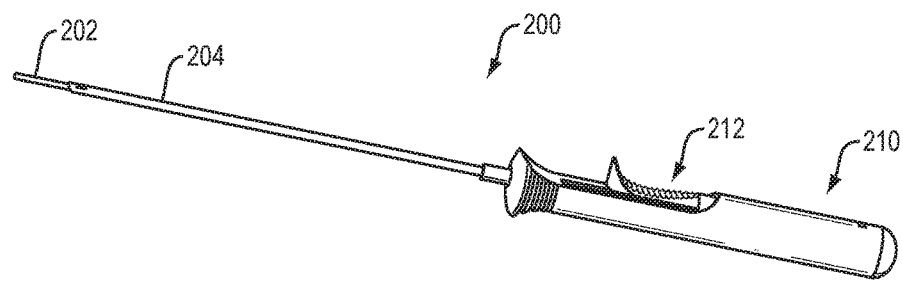
FIG. 4A is a perspective view of a surgical device that can be used with the modular suture anchor delivery device of the present invention.
Figure 4B:
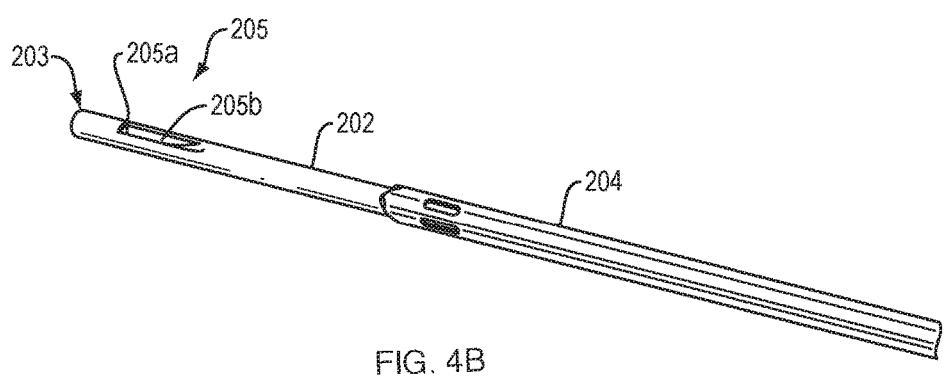
FIG. 4B is one exploded view of the distal tip region of the surgical device of FIG. 4A when in the open position.
Figure 4C:
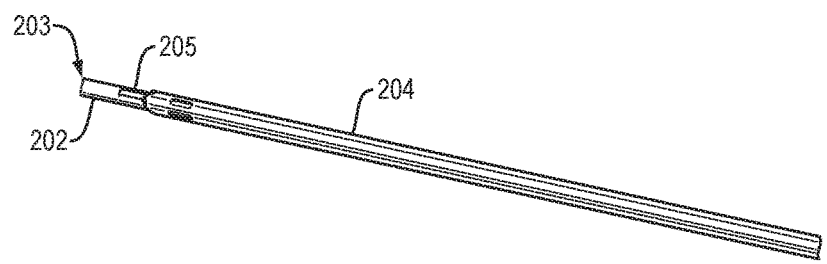
FIG. 4C is another exploded view of the distal tip region of the surgical device of FIG. 4A when in the closed position.
Figure 6:
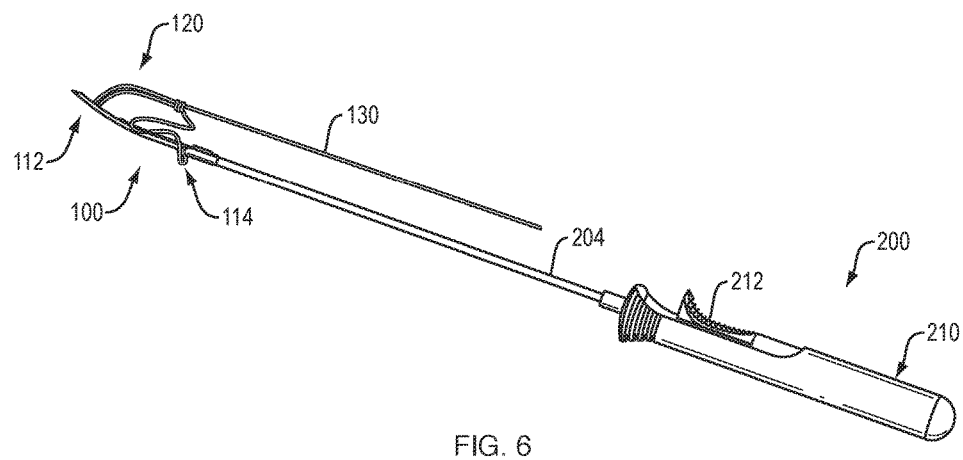
FIG. 6 is another perspective view of the suture anchor delivery device of FIG. 1 when mounted on the other surgical device, including an exploded partial view showing the anchors that would be mounted to the delivery device.
Figure 7:
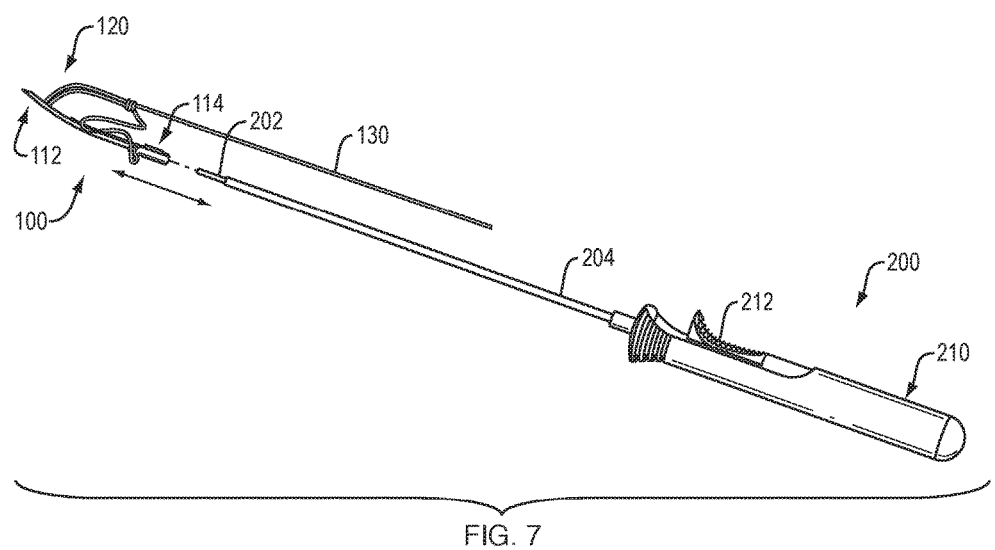
FIG. 7 is another perspective view illustrating an embodiment of the suture anchor delivery device when separated from the other surgical device.

Referring now to the various figures of the drawing wherein like reference characters refer to like parts, there is shown in FIGS. 1-3 various views of an implant/anchor deployment device/module 100 according to the present invention as well as features thereof, and there is shown in FIGS. 6-7 various views of such an implant/anchor deployment device/module 100 when mounted on a surgical device, more specifically a suture cutter as is known in the arts, such as the suture cutter that is shown in FIGS. 4A-C.

Referring now to FIGS. 4A-C, there is shown perspective view of a surgical device that can be used with the modular suture anchor delivery device of the present invention (FIG. 4A); an exploded view of the distal tip region of the surgical device of FIG. 4A when in the open position (FIG. 4B) another exploded view of the distal tip region of the surgical device of FIG. 4A when in the closed position (FIG. 4C). In the illustrated embodiments, such a surgical device includes a suture cutter device 200 that typically includes two concentrically disposed members, an inner member 202 and an outer member 204 that are movable with respect to each other. The suture cutter device 200 also includes a handle 210 to which the two concentrically disposed members are operably coupled. These members can be tubular or other shape known in the art.

In the illustrated embodiment, the inner member 202 is maintained in fixed relation to the handle 210 and the outer member 204 is movably coupled to the handle 210. More particularly, the outer member 204 is coupled or connected to a slide mechanism 212 that is movably disposed in the handle 210. The outer member 204 and slide mechanism 212 are coupled such that movement of the slide mechanism in one direction (backwards) draws the end of outer member towards the handle so as to be in an open position as shown in FIG. 4B and so that movement of the slide mechanism in a second or opposite to the one direction (forward) urges the end of outer member towards the distal end of the inner member so as to be in a relatively closed position as shown in FIG. 4C. It should be recognized that such an arrangement is not limiting. Thus for example, the outer member 204 could be arranged and configured so as to be in fixed relation with the handle and the inner member 202 could be arranged and configured so as to be movable in either of two directions (e.g., two opposing directions).

In such a suture cutter device 200, one member (e.g., the inner member 202) is typically used to grab and hold the suture and the other member (e.g., the outer member 204) is typically moved with respect to the "one member" or inner member so as to cut the suture in guillotine fashion. For example, the cutter device outer member or sleeve is moved axially to expose the portion of the inner member that grabs the suture and is again moved axially in an opposite direction so as to cut the grabbed suture. As is known to those skilled in the art, in such grabbing the end of the suture is passed through an opening or aperture in the distal end of the inner member 202 such that the suture exits into and out of the depressed region 205 also provided in the inner member. As described further herein, the inner and outer members 202, 204 of such a suture cutter device 200 are used by the implant/anchor deployment device/module 100 according to the present invention so that the implant/anchor deployment device/module 100 can be secured to the cutter device and so the implants/anchors can be deployed.

Figure 1B:
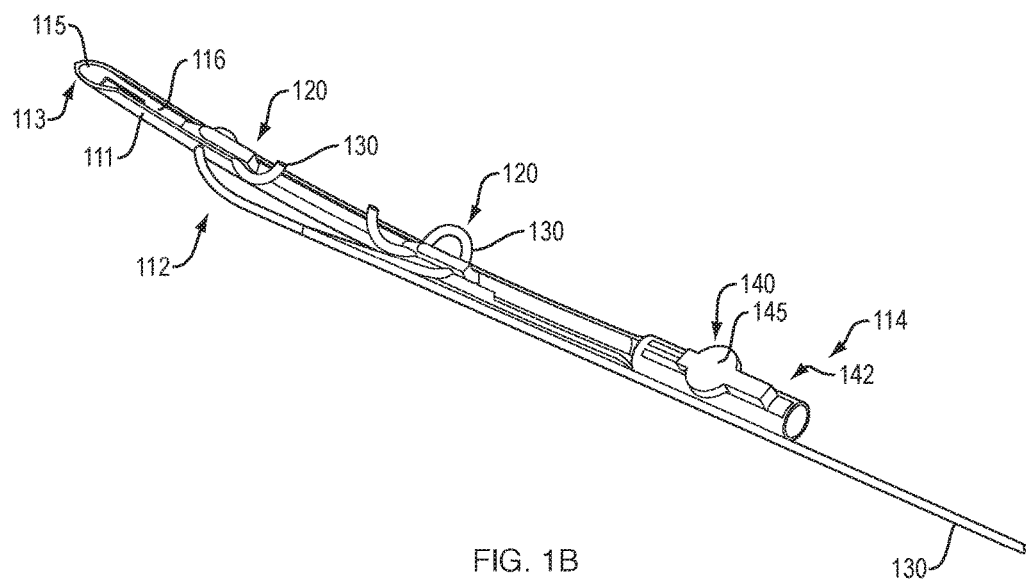
FIG. 1B is another perspective view of a modular suture anchor delivery device according to the present invention with suture and suture anchors.
Figure 1C:
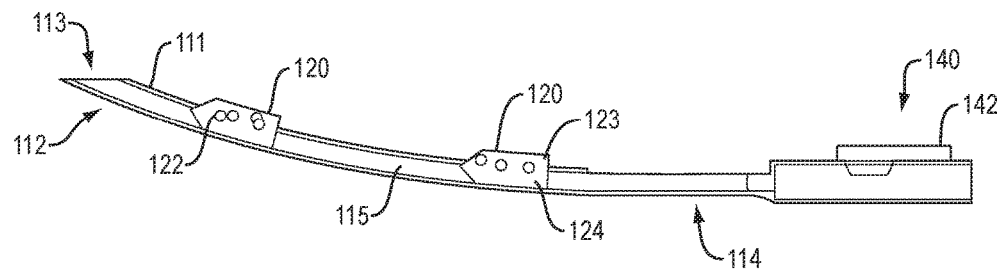
FIG. 1C is a cross-sectional side view of a modular suture anchor delivery device with suture anchors.
Figure 1D:
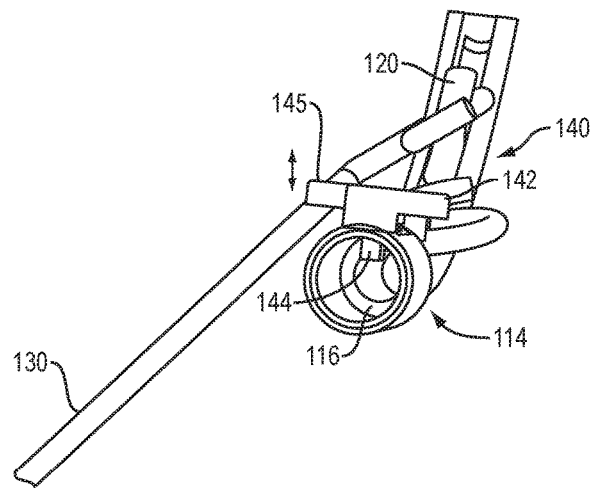
FIG. 1D is an end view of a modular suture anchor delivery device according to the present invention such as that shown in FIG. 1B.
Figure 1E:
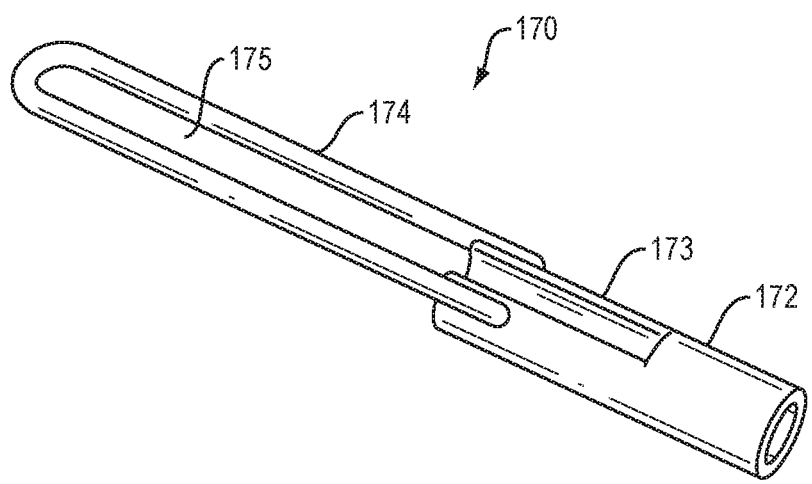
FIG. 1E is a perspective view of a sleeve member for a modular suture anchor delivery device according to the present invention.
Figure 1F:
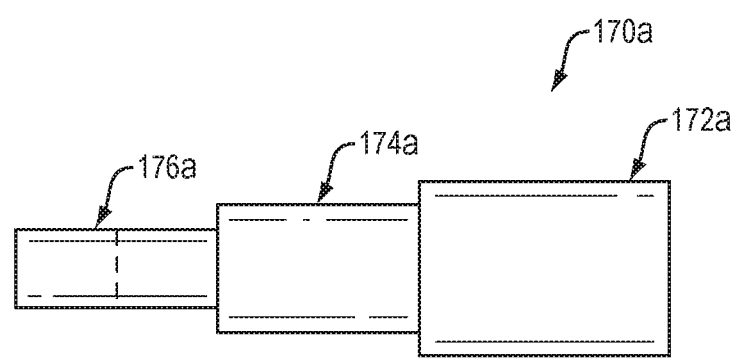
FIG. 1F is a schematic view of a sleeve member.

Referring now to FIGS. 1-3, there is shown a perspective view of a modular suture anchor delivery device 100 without the suture anchors (FIG. 1A); another perspective view of a modular suture anchor delivery device with suture and suture anchors (FIG. 1B); a cross-sectional side view of a modular suture anchor delivery device with suture anchors (FIG. 1C); an end view of a modular suture anchor delivery device such as that shown in FIG. 1B (FIG. 1D); a perspective view of a sleeve member for a modular suture anchor delivery (FIG. 11E); a schematic view of a sleeve member (FIG. 1F); a perspective view of a modular suture anchor delivery device without suture anchors and including functionalities of the surgical device (FIG. 2A); an exploded side view of a modular suture anchor delivery device and including functionalities of the surgical device (FIG. 2B) and another perspective view of the modular suture anchor delivery device when coupled or attached to the end of the surgical device (FIG. 3). Such an implant/anchor deployment device/module 100 includes a body 110 having a distal end portion 112 and a proximal end portion 114. For convenience, the implant/anchor deployment device/module 100 shall be hereinafter referred to using the term "anchor deployment module 100," however, the shortened descriptor shall not be assumed as altering the scope of the present invention as to such a module or device.

Reference in the following discussion also shall generally be made to a suture cutter, however, this also shall not be considered limiting as this term shall be understood to be inclusive of any conventional surgical device that can be used in surgical procedures and usable with the implant deployment module 100 of the present invention to deliver and deploy implants/anchors. Further, the terms implant(s), anchor(s) or suture anchor(s) in the following discussion also shall be understood to relate or correspond to the term "implant/anchor" unless otherwise indicated.

The tip 113 or end of the distal end portion 112 is configured or shaped so as to appropriate for the intended use and for the particular surgical procedure being followed, such as for example, the tissue the tip is to be inserted into or pass through. In illustrative embodiments, the tip 113 is a sharp or atraumatic tip that is used to pierce or penetrate body tissue (e.g., meniscus). Additionally, at least a segment or portion of the proximal end portion 114 is configured and arranged so that the anchor deployment module 100 can be removably secured to the suture cutter 200 or other conventional surgical device.

The distal end portion 112 also is configured so as to receive one or more anchors 120 that are intended for deployment therefrom in accordance with the particular surgical or treatment protocol/procedure being followed or implemented. The distal end portion 112 or at least the segment thereof containing the suture anchors 120 includes a slot 116 in the outer surface 111 thereof, which extends through the body member into the lumen 115 (e.g., a slotted aperture). The lumen 115 and the slot 116 both extend along the length or long axis of the distal end portion. The lumen and/or slot also can be arranged so as to extend along the entire length of the body member 110 including the proximal end portion 114.

The lumen 115 and slot 116 in the area of the distal end portion 112 are further configured and arranged so that each of the one or more suture anchors 120 are movably received therein. More particularly and as shown, a first portion 124 of each suture anchor 120 is movable received in the lumen 115 and a second portion 123 of the suture anchor extends through the slot and outwardly from the slot and above the outer surface 111 of the body 110. More specifically, the suture anchor first portion 124 within the lumen is configured so as to be larger than the slot so that the first portion remains movably disposed within the lumen.

The suture anchor second portion also is preferably configured so that it receives (e.g., movably receives) and holds a suture 130 (e.g., at least one suture for each anchor). For example and as shown in FIGS. 1-2, the suture anchor second portion includes one or more apertures 122 through which a suture can be inserted and received by the second portion. Additionally and as is known in the arts, the suture 130 can be arranged in any of a number of ways. In particular and with reference to FIG. 1B and FIG. 3, the suture 130 can be arranged such that it extends between and through both suture anchors 120 and so that once the suture anchors 120 are deployed the suture can be tightened so as to, for example, treat the damaged tissue (e.g., draw the opposing edges of the damaged meniscus towards each other). In further embodiments, and as shown in FIGS. 1B and 1C, each suture anchor can include a plurality of such apertures 122 and the suture can be threaded through the plurality of apertures so as to secure the suture to a given suture anchor. In exemplary embodiments, the suture(s) 130 is/are pre-tied and arranged such that when the surgeon applies a longitudinal force to an end of a suture this shortens the suture and tightens the knot.

While two suture anchors 120 are illustrated, it should be recognized that the distal end portion 112 can be arranged so as to have any number of implants/anchors thereon, for example, one such suture anchor, one or more such suture anchors, a plurality of such suture anchors or a multiplicity (e.g., 3-6 or more) of such suture anchors. As each of the suture anchors 120 are movably disposed within the distal end portion 112, each of the suture anchors can be deployed, passively or actively, from the distal end portion 112 and the tip 113 thereof as described further herein. Also and as further described herein, such suture anchors 120 can be moved on the distal end portion 112 from a stored position, an initial position or some intermediate position, to a pre-deployment position that is closer to the tip 113 or end of the distal end portion than the stored position.

The proximal end portion 114 of the body 110 is configured and arranged so as to receive a portion of the structure of the surgical device to which it is to be attached/coupled to, so that the anchor deployment module 100 can be removably secured to the surgical device. In this way, the proximal end portion 114 can be adapted so it can be secured to a given structural feature or functionality of the surgical device.

In more particular aspects/embodiments, the proximal end portion 114 of the body 110 is configured and arranged so as to receive a portion of the structure of the suture cutter 200 so that the anchor deployment module 100 can be removably secured to the suture cutter. In illustrative embodiments, the proximal end portion 114 is configured and arranged using any of a number of techniques known to those skilled in the art, so as to be removably secured to one of the inner member 202 or outer member 204 of the suture cutter. In more specific illustrative embodiments, the proximal end portion 114 is removably secured to the suture cutter inner member 202.

In yet more illustrative embodiments, at least a segment or portion of the proximal end portion 114 includes a structure that complements the portion of the suture cutter to which the proximal end portion is being secured thereto. In more particular embodiments, the structure of the suture cutter portion is a tubular or cylindrical member, such as that depicted for either the inner or outer members 202, 204, and the complimentary structure of the proximal end portion 114 includes a pocket or socket 117 (e.g., cylindrical pocket or socket) configured for receiving one of the inner and outer tubular members of the suture cutter. More particularly, the complimentary structure of the proximal end portion 114 includes an open ended pocket or socket 117 that is sized and shaped to removably receive (e.g., slidably receive) the distal end 203 of the inner member 202 of the suture cutter 200.

As described further herein, such a socket 117 also is configured so as to limit axial movement of the suture cutter distal end 203 in at least one direction when it is secured to the proximal end portion. More particularly and as further described herein, the depth of the socket is established so as to limit axial movement of the suture cutter/inner member distal end 203 in at least one direction when it is secured to the proximal end portion and the cross-section of the socket is established to minimize widthwise or radial movement of the suture cutter distal portion.

In further embodiments, the anchor deployment device 100 and surgical device 200 further include a mechanism 140 that cooperates with the open ended socket 117 so as to removably secure the inner member distal end 203 within the open ended socket. As indicated herein, such a mechanism can embody or use any of a number of techniques known to those skilled in the art for accomplishing such a function.

In more particular embodiments, such a mechanism 140 includes a securing mechanism 142 that is coupled to the open ended socket 117 or proximal portion 114 of the anchor deployment device and a complementary mechanism that is provided on the surgical device, more particularly the inner member distal end 203 thereof. In use the securing mechanism engages the complementary mechanism so as to secure or couple the inner member distal end to the body member proximal end portion 114 (e.g., within the open ended socket 117) and so that the inner member distal end remains coupled or attached to the body member proximal portion (e.g., not withdrawn from the open ended socket 117) during normal manipulation of the coupled devices during at least the insertion, delivery and deployment of the suture anchor(s) 120.

In yet further exemplary embodiments, the securing mechanism 142 includes a structure that is secured, coupled, attached or integrally formed with the body member proximal end portion 114, more particularly the open ended socket 117 thereof, and which is arranged so that a portion of the securing mechanism removably engages the complementary mechanism of the inner member. More particularly, a portion of the securing mechanism is configured and arranged so as to extend through an opening 117 (e.g., slot, aperture) in the body member proximal end portion 114 and into the lumen 115.

In this way, when the inner member distal end 203 is inserted into the open ended socket 117, this securing mechanism portion engages the complimentary mechanism of the surgical device (e.g., inner member) thereby removably securing the surgical device 200 to the anchor deployment device. As indicated herein, such engagement inhibits/minimizes at least any axial movement of the inner member in the direction of withdrawal of the suture cutter distal end from the open ended socket. As also indicated herein, the open ended socket also is configured (e.g., sized) so to also inhibit/minimize any axial movement of the inner member in the opposite direction (i.e., opposite to withdrawal of the suture cutter distal end from the open ended socket).

In exemplary illustrative embodiments, the securing mechanism 142 forms a latching type of mechanism that latches to or removably engages the surgical device distal end or suture cutter inner member so as to restrain axial movement in the direction of withdrawal. More particularly, the securing mechanism 142 includes a cantilevered structure 143 that is coupled, attached or otherwise formed integral with the body member proximal end portion 114, more particularly the open ended socket 117 thereof. Such a cantilevered structure 143 also includes a protrusion 144 or prong like element that extends outwardly therefrom and so as to extend inwardly through the slot 117 or opening and into the open ended socket such as shown in FIG. 1D. The cantilevered structure 143 also is arranged so as to bias the protrusion 144 in the inwardly direction so that the protrusion engages the complimentary mechanism of the inner member and remains engaged during manipulation of the combined surgical device and anchor deployment device.

The securing mechanism 140 also includes a manipulating portion 145 that is configured to allow a surgeon to manipulate the cantilevered structure 143 so the protrusion 144 can be disengaged from the complimentary mechanism of the inner member. For example, the manipulating portion 145 can be configured and arranged so as to allow the surgeon to move the protrusion 144 in an outwardly direction out of engagement with the complimentary mechanism thereby allowing the surgical device to be withdrawn from the open ended socket 117. In an illustrative embodiment, the manipulating portion 145 forms a structure that can be grasped by the surgeon during a procedure (e.g., round button shaped member). In yet further aspects/embodiments and as further described herein, the securing mechanism 140 also is configured and arranged so that it does not interfere with movement of a movable sleeve 170.

As to the complimentary mechanism, such a mechanism includes an opening, artifact (e.g., surface artifact), depressed region, aperture or the like that is provided in the surgical device, either for the device's intended function or for purposes of engaging with the anchor deployment device 100 as described herein. In exemplary, illustrative embodiments, such as when the surgical device is a suture cutter as is known in the arts, the complimentary mechanism includes a depressed region 205 (e.g., see FIG. 4B), provided in the inner member distal end 203 of such a suture cutter.

As is known to those skilled in the art, a conventional suture cutter can be configured with an axially extending aperture or lumen in the distal end also extends inwardly from the distal end to the depressed region. In use, an end of the suture is introduced into this axially extending aperture such that it extends into and typically out of the depressed region 205. After the suture has been drawn to the desired extent into the depressed region, the outer member 202 is manipulated so as to cut the suture in guillotine fashion.

In illustrative embodiments, such a depressed region 205 can include a front wall 205a and a bottom surface 205b. In use, when the protrusion 144 extends inwardly to engage the complimentary mechanism, the protrusion is received in the depressed region 205 and so as to be disposed in proximity to the front wall 205a, thereby at least limiting the axial movement of inner member in the withdrawal direction. In further embodiments, an end surface of the protrusion is resting on or is spaced from the bottom surface 205b.

Such a bottom surface 205b also can be arranged so as to slope upwardly towards the back end of the depressed region 205 (e.g., such as to facilitate movement of the suture end). As described herein, the depth of the open ended socket 117 can be adjusted or set so as to limit movement of the inner member in the direction opposite to the direction of withdrawal. More specifically, the depth of the open ended socket is set or adjusted so as to prevent the protrusion 144 from becoming disengaged from the depressed region 205 by sliding up such a sloped surface.

In the illustrated embodiment, the open ended socket 117 is depicted as being formed from an essentially solid structure, however, this is not limiting as it also is within the scope of the present invention to form or establish such an open ended socket using any of a number of techniques known to those skilled in the art. For example, such an open ended socket can be made up of a framework of members that when combined and arranged define the general shape and size of the open ended socket. Also, such a framework can be configured so as to include open areas between the members forming the framework. Such an open ended socket also is preferably established so that the surgical device has limited movement in the radial direction.

In yet further embodiments, such an anchor deployment device 100 further includes a movable sleeve 170 that is configured and arranged so as to be movably disposed about the body member 110, more particularly about the proximal end portion 114 thereof (see FIG. 2A). More particularly, such a movable sleeve 170 includes a first portion 172 and a second portion 174 extending from the first portion in a generally axial direction. In addition, the second portion is secured in any of a number of fashions to the first portion (e.g., adhesives, vibrational welding, brazing etc.).

The movable sleeve 170 is movable axially about the body member and proximal end portion 114 so that when it is moved in a first direction towards the tip 113 of the distal end portion 112, the movable sleeve, more particularly, the sleeve second portion 174 contacts at least one of the anchors 120. Further movement of the movable sleeve 170 in the first direction advances the anchor(s) from their initial or stored position to any of a number of other positions including a pre-deployment position. In alternative embodiments, when the anchor deployment device 100 is assembled in its final form, the anchor 120 closest to the tip 113 can be located in the pre-deployment position. After deployment of the anchor arranged closest to the tip, the surgeon can use the movable sleeve 170 to move the next closest anchor into the pre-deployment position.

As indicated above, the securing mechanism 140 is configured and arranged so that it does not interfere with movement of a movable sleeve 170, as the securing mechanism is such that it extends outwardly and thus above the proximal end portion 114 of the body member 110. In yet further aspects/embodiments, the movable sleeve 170 and the securing mechanism are respectively configured so as to minimize the lateral profile of the securing mechanism and so that the movable sleeve is structured so it passes by the securing mechanism. More particularly, the movable sleeve first portion 172 is arranged with an axially extending slot 117, aperture or opening that is sized and arranged so that a portion of the securing mechanism 142 extending above the body member proximal portion is slidably received in the axially extending slot 173.

In addition, the movable sleeve second portion 174 also is configurable so that the portion of the securing mechanism 142 extending above the body member proximal portion also is slidably received therein. In exemplary illustrative embodiments, the movable sleeve second portion 174 is a cylindrical member that is hooped shaped having an open area 175 disposed within the hoop. This open area 175 is established so that the portion of the securing mechanism 142 extending above the body member proximal portion is movably received therein. This structure is not limiting as it is within the scope of the present invention, for the movable sleeve second portion 174 to form any of a number of structures as are known to those skilled in the arts that has sufficient axial rigidity to move the anchor(s) in the described manner as well as to avoid contacting the securing mechanism while the sleeve moves axially. For example, the movable sleeve second portion 174 could be in the form of a partial hoop or partial box shape (e.g., two or three sides of a box shape).

The movable sleeve second portion 174 also is arranged so as to be secured to the movable sleeve first portion such that axial movement of the first portion also is imparted to the second portion. In particular embodiments, the length of the second portion is established such that when the second portion is moved axially by the first portion such axial movement is imparted to each of the anchor(s) on the body member distal end portion. More specifically, the second portion 174 imposes an axial force on the anchor closest to the second portion which in turn imparts an axial force on an anchor closer to the distal end 113. Such axial forces can be used to move the anchors from any position (e.g., initial, stored or intermediate) so that the anchor closet to the distal end 113 is disposed in a pre-deployment position.

As indicated herein, an anchor 120 may be deployed from the anchor deployment device 100 either passively or actively (i.e., by application of a force). In the case of passive deployment, when the closest anchor is in the pre-deployment position, the anchor is withdrawn from the distal end portion 112 as the anchor 120 interacts with the tissue during a withdrawal motion of the anchor deployment device. For example, when the suture anchor is to be deployed along the backside of the meniscus, the suture anchor (e.g., second portion 122 thereof) interacts with the meniscal tissue as the anchor deployment device is being drawn back through the meniscal tissue leaving the anchor along the backside of the meniscus.

In active deployment, the surgeon takes some action that applies a force to the anchor so that it is pushed out of the distal end portion 112. For example, the movable sleeve 170 can be dimensioned or otherwise configured (e.g., the second portion 174 thereof) so as cause the closest anchor to be pushed out of the distal end portion when the sleeve is pushed further in the first direction. In alternative embodiments, the anchor deployment device 100 is arranged so as to include a member that acts on the anchor causing it to be deployed responsive to some action of a functionality under the control of the surgeon.

In more particular embodiments (see FIG. 2B), the movable sleeve 170 is operably coupled to the suture cutter outer member 204 such that movement of the outer member responsive to the action of the slide mechanism 212 causes the movable sleeve to move in the first direction. In yet more particular embodiments, a member or rod (e.g., pushrod 214) is coupled to the outer member 204 and the slide mechanism 212 and is arranged so the slide mechanism moves the pushrod in an axial direction responsive to movement of the slide mechanism. The pushrod 214 also is configured and arranged so that it acts on the movable sleeve 170, more particularly the movable sleeve first portion 172, and thus also causes the movable sleeve to move axially in the first direction responsive to the movement of the pushrod towards the distal end portion.

In illustrative exemplary embodiments (see FIG. 2B), the pushrod 214 is configured so as to include a stepped region 215 that extends in a vertical direction a sufficient distance so that it engages an end surface of the movable sleeve first portion 172 so as to thereby move the movable sleeve 170 in the first direction. In yet further embodiments, the proximal end portion 114 is configured so as to include a slotted opening in which is movably received the stepped region 215 of the pushrod 214. This slotted opening extends along the long axis of the proximal end portion 114 a sufficient distance so as to allow the pushrod 214 to move the next closest or the second anchor from its initial position to the pre-deployment position. In further embodiments, the slotted opening includes an end surface that restrains further axial movement of the stepped region, the pushrod and thus the sleeve in the axial direction when the deployment device is coupled to the surgical device. In particular embodiments, the end surface is located so it corresponds to one of the pre-deployment position or a position corresponding to an active deployment of the anchor.

Referring now to FIG. 1F there is shown a schematic view of an alternative embodiment for a movable sleeve 170a according to the present invention. Such a movable sleeve 170a includes a first portion 172a, a bridging or second portion 174a and a pushing member 176a. The first portion 172a is operably coupled, attached or secured to the bridging/second portion 174a so that axial movement of the first portion is imparted to the bridging/second portion and the bridging/second portion is operably coupled, attached or secured to the pushing portion 176a so that axial movement of the first portion which is imparted to the bridging/second portion is also imparted to the pushing member. Reference shall be made to the foregoing discussion as to details for the first and second portions except as otherwise provided herein.

The bridging or second portion 174a is established, configured and arranged so that it bridges the distance between the first portion and pushing member 176a so that the pushing member can push against the anchor(s) so as to move them in the fashion described above for the second portion 174. As such, the bridging or second portion 174a is such as to have sufficient rigidity to move the pushing member and have a configuration that avoids interfering with the securing mechanism.

The pushing member 176a can have any of a number of configurations that are sufficient to cause movement of the anchor(s) responsive to axial movement of the movable sleeve 170. In one embodiment, the pushing member 176a is arranged so as to extend from the bridging/second portion 174a so to engage an end surface of an anchor second portion 123 such as that described above for the second portion of FIG. 1E. In another embodiments, the pushing member 176a is configured so as to include a first segment and a second segment that are joined together. The second segment is arranged so as to be slidable disposed in the lumen 115 such that an axial force being applied to the pushing member is applied or imparted to an anchor first portion 124 that also is disposed in the lumen. The first segment is secured between the bridging/second portion and the second segment so that an axial force applied to the second portion is imparted to the second segment. The first segment also is configurable so as to accommodate for any axial differences between the bridging/second portion and the second segment.

As indicated herein, the present invention also features a surgical device kit 300 or device kit that includes one or more anchor deployment devices 100a-c according to the present invention as well as one or more surgical devices such as slotted cannula or introducer 310 and the surgical device to which the one or more deployment devices can be operably coupled. As indicated above, such a surgical device can be a suture cutter 200 as is known to those skilled in the art. Such a device kit 300 is particularly advantageous as it allows a surgeon to utilize the modularity concept embodied in such anchor deployment devices to best effect while minimizing part counts and costs associated with the surgical procedure being performed.

In particular, such a device kit 300 can be arranged so it can provide any of a number of configurations of such anchor deployment devices for such use during a surgical procedure. For example, the provided anchor deployment device can be configured such that the anchor deployment device or the distal portion 112 thereof provide any of a number of suitable geometries including an anchor deployment device 100a having a straight distal end portion 112a, an anchor deployment device 100b having a distal end portion 112b that is curved in one direction and an anchor deployment device 100c having a distal end portion 112c that is curved in another direction. These geometrical configurations are illustrative as it is within the scope of the present invention to provide distal end portions 112 that are configured and arranged: (a) so as to be curved and have any degree of curvature, (b) a distal end portion whose long axis is at an angle with respect to the long axis of the proximal end portion, and (c) distal end portions that form a three dimensional shape or structure. Such different geometrical configurations provide a mechanism by which a surgeon can select a configuration that is best suited, when it is secured to a surgical device, for allowing the selected anchor deployment device to enter the body and for navigating the distal end portion 112 so that it is located proximal or at the targeted tissue site and also allow the surgeon to thereafter deploy the anchor at such a site.

The modularity of such anchor deployment devices 100 also allows one to create surgical kits that have some level of customization. For example, in anticipation of deploying a number of suture anchors, the surgical device kit can be arranged so as to include a plurality or a multiplicity (e.g., 3-6 or more) of anchor deployment devices having similar or the same geometry that would be appropriate for the surgical procedure (e.g., all straight geometries). In this way, the surgeon could select a device kit having anchor deployment devices with the desired geometry and thereafter during the procedure connect and de-connect the individual anchor deployment devices as needed to/from the surgical device so that the desired number of suture anchors can be deployed.

As the anchor deployment devices of the present invention are to be used in combination with an existing surgical device that is not specifically configured for the deployment of suture anchors, there is no need to create a unique device for such deployment. This reduces part count and allows the use of one surgical device to perform more than one function during the procedure. This also can lead to reduced expenses associated with the surgical procedure because a unique anchor deployment device is not required as well as that the anchor deployment device is a module and thus should be less costly than providing a unique device.

Referring now also to FIGS. 6-7 and as also indicated herein, the present invention also features methods for deploying suture anchors 120 using the anchor deployment device of the present invention. Such methods include selecting a suitable anchor deployment device 100, 100a-c from the surgical device kit 300 for use during a given surgical procedure. In particular, selecting an anchor deployment device having the appropriate geometry or configuration for facilitating entry into the body (e.g., the knee joint) and its navigation to a desired targeted tissue site as well as suture anchors 120 and sleeve 170.

After selecting the desired anchor deployment device 100, the surgeon or other surgical personnel slides the anchor deployment device 100, 100a-c over the distal end of the surgical device (e.g., suture cutter 200) so as to connect the anchor deployment device to the surgical device distal end. More particularly, when the surgical device is a suture cutter 200, the inner member 202 of the suture cutter is coupled to the proximal end portion 114 of the anchor deployment device 100. More specifically, the distal end 203 of the suture cutter inner member 202 is inserted into a socket 117 or other structure at the proximal end portion 114 of the anchor deployment device 100 such that a securing mechanism 140 removable couples or connects the suture cutter and the anchor deployment device to each other. The surgeon also can takes such other action(s) as may be necessary for the later deployment of the anchors (e.g., moving the closest anchor to the pre-deployment position).

Using the suture cutter 200 as a manipulation platform, the surgeon manipulates the suture cutter so as to also thereby manipulate the anchor deployment device such that the coupled devices are appropriately inserted into the body (e.g., knee joint). The surgeon continues to manipulate the suture cutter so as to further navigate the anchor deployment device so the distal end portion 112 thereof is located at or proximal a targeted tissue site, such as for example, the meniscus. Thereafter, the surgeon takes those additional actions that are require so that an anchor 120 is appropriately positioned for deployment at a desired location. For example, when the tissue to be treated is the meniscus, the surgeon still using the suture cutter 200 causes the anchor deployment device 100 to pierce and pass through the tissue (e.g., the meniscus) to a location where a suture anchor 120 is to be deployed.

After positioning the distal end portion at a desired location, the surgeon takes the appropriate actions to deploy the suture anchor 120. For example, in the case of a passive deployment the surgeon manipulates the surgical device so as to cause the suture anchor 120 to be withdrawn from the distal end portion such as by the interaction of the suture anchor with the tissue. In the case of active deployment, the surgeon takes the appropriate action that causes the suture anchor to be moved out of the distal end portion (e.g., applying a force to the suture anchor thereby causing it to move out of the distal end portion).

If there is another suture anchor to be deployed, then the surgeon withdraws at least the distal end portion 112 from the targeted tissue and thereafter causes the second suture anchor to be moved on the distal end portion to the pre-deployment position as described herein. When the second suture anchor is so-located at the pre-deployment position, the surgeon again manipulates the suture cutter so as to cause the distal end portion of the anchor deployment device to be located at another targeted tissue site. Thereafter, the surgeon still using the suture cutter 200 causes the anchor deployment device 100 (e.g., distal end portion thereof) to be appropriately positioned at a location where the next suture anchor 120 is to be deployed. The surgeon then repeats the above described process for deploying the suture anchor and withdrawing the distal end portion.

If additional suture anchors are to be deployed and there are no more suture anchors located/disposed on the distal end portion, the surgeon withdraws the combined suture cutter and anchor deployment device from the body. The surgeon or other surgical personnel then detaches the used or emptied anchor deployment device from the suture anchor, selects another loaded anchor deployment device and attaches the loaded anchor deployment device to the surgical device/suture cutter. The surgeon then repeats the above-described process for locating, positioning and deploying the additional suture anchors.

If there are no more suture anchors to be deployed, the surgeon withdraws the combined suture cutter and anchor deployment device from the body. The surgeon or other surgical personnel then detaches or removes the used or emptied deployment device from the surgical device/suture cutter. Thereafter, the surgeon can use the decoupled surgical device in the intended manner. For example, if the surgical device is a suture cutter, then the surgeon can use the de-coupled suture cutter to cut excess length of a suture(s) such as the suture(s) that may have been provided with the suture anchors. As indicated herein, the surgeon would take such other actions as may be necessary to tighten the sutures in accordance with the surgical procedures.

Although a preferred embodiment of the invention has been described using specific terms, such description is for illustrative purposes only, and it is to be understood that changes and variations may be made without departing from the spirit or scope of the following claims.

INCORPORATION BY REFERENCE

All patents, published patent applications and other references disclosed herein are hereby expressly incorporated by reference in their entireties by reference.

EQUIVALENTS

Those skilled in the art will recognize, or be able to ascertain using no more than routine experimentation, many equivalents of the specific embodiments of the invention described herein. Such equivalents are intended to be encompassed by the following claims.

What is claimed is:

1. A suture anchor deployment system comprising:
   a surgical device; and
   at least one deployment device, each of said at least one deployment device including:
   a body member having a proximal end portion and a distal end portion the body member comprising a lumen extending along a length of the body member and a slot extending through an outer surface of the distal end portion into the lumen;
   a socket extending through the proximal end portion;
   a plurality of suture anchors disposed within the lumen at the body member distal end portion;
   a suture extending between each of the plurality of suture anchors; and
   a securing mechanism coupled to the socket such that a portion of the securing mechanism extends through the socket and into the lumen, the securing mechanism being separate and distinct from the suture;
   wherein the securing mechanism is configured so as to be removably attached to a first end portion of the surgical device: and
   wherein the surgical device is a suture cutter having a movable outer member and an inner member, the inner member being removably attached to the body member proximal end portion.

2. The system of claim 1, wherein
   the body member proximal end portion is further configured so as to be removably attached to an opposing structure of the inner member of the surgical device.

3. The system of claim 2, wherein the proximal end portion of the body member is further configured so as to include an enlarged portion for receiving therein the opposing structure of the inner member.

4. The system of claim 2, wherein:
   the outer member includes a lumen extending along a long axis;
   the inner member is disposed within the outer member lumen; and
   the inner and outer in embers are movable with respect to each other.

5. The system of claim 4, wherein the outer member is movable along the long axis with respect to the inner member.

6. The system of claim 4, wherein movement of the outer member along the long axis in one direction moves each of the plurality of anchors to a pre-deployment position.

7. The system of claim 4, wherein, after deployment of a first one of the plurality of anchors, movement of the outer member along the long axis in one direction causes a second one of the plurality of anchors to be moved to a pre-deployment position.

8. The system of claim 1, wherein a tip of the body member distal end portion is configured for insertion into tissue.

9. The system of claim 1, further comprising a plurality of deployment devices, wherein the distal end portion of each body member is further configured so as to have a given geometry selected for facilitating navigation of the distal end portion to a targeted area and wherein the geometry of at least one body member distal end portion is different from the geometry of another body member distal end portion.

10. The system of claim 1, wherein a first portion of each of the plurality of suture anchors is movably received within the lumen and a second portion of each of the plurality of suture anchors extends through the slot above the outer surface.

11. The system of claim 10, wherein the second portion of each of the plurality of suture anchors includes one or more apertures configured for the passage of the suture.

12. A method for deploying a suture anchor during a tissue repair procedure, the method comprising the steps of:
providing at least one deployment device and a surgical device; wherein each of the at least one deployment device includes:
a body member having a proximal end portion and a distal end portion, the body member comprising a lumen extending along a length of the body member and a slot extending through an outer surface of the distal end portion into the lumen;
a socket extending through the proximal end portion;
a plurality of suture anchors disposed within the lumen at the body member distal end portion;
a suture extending between each of the plurality of suture anchors; and
a securing mechanism coupled to the socket such that a portion of the securing mechanism extends through the socket and into the lumen, the securing, mechanism being separate and distinct from the suture;
wherein the surgical device is a suture cutter having a movable outer member and an inner member;
removably securing the securing mechanism to the inner member of the surgical device;
inserting the deployment device and at least a portion of the surgical device into tissue;
locating the body member proximal end portion at a desired location within the tissue; and
deploying at least one of the plurality of anchors from the body member distal end portion.

13. The method of claim 12, wherein said method further includes manipulating the surgical device, after said locating the body member distal end portion, so that the distal end portion passes through the tissue.

14. The method of claim 13 wherein said deploying includes deploying the at least one of the plurality of anchors after said manipulating.

15. The method of claim 12, wherein, after completing deploying the at least one of the plurality of anchors, said method further includes de-connecting the body member proximal end portion from the inner member of the surgical device, thereby allowing the surgical device to thereafter perform a procedure not directly related to deployment of the at least one of the plurality of anchors.

16. The method of claim 12, wherein the body member proximal end portion is further configured so as to be removably attached to an opposing structure of the inner member of the surgical device; and wherein removably securing includes removably securing the body member proximal end portion to the opposing structure of the inner member.

* * * * *